United States Patent [19]
Hoshino et al.

[11] Patent Number: 6,127,156
[45] Date of Patent: Oct. 3, 2000

[54] D-SORBITOL DEHYDROGENASE GENE

[75] Inventors: Tatsuo Hoshino, Kamakura; Taro Miyazaki; Setsuko Ojima, both of Fujisawa; Masako Shinjoh, Kamakura; Noribumi Tomiyama, Fujisawa, all of Japan

[73] Assignee: Roche Vitamins Inc., Parsippany, N.J.

[21] Appl. No.: 09/136,251

[22] Filed: Aug. 19, 1998

[30] Foreign Application Priority Data

Aug. 21, 1997 [EP] European Pat. Off. .............. 97114432

[51] Int. Cl.⁷ .............................. C12N 9/04; C12N 1/20; C12P 21/06; C07H 21/04
[52] U.S. Cl. ...................... 435/189; 435/190; 435/252.3; 435/252.33; 435/320.1; 435/69.1; 530/350; 536/23.2; 536/23.1; 536/23.7
[58] Field of Search ................................. 435/189, 252.3, 435/252.33, 320.1, 69.1, 190; 536/23.2, 23.7; 530/350

[56] References Cited

U.S. PATENT DOCUMENTS 5,747,301  5/1998  Hoshino et al. ........................ 435/105

FOREIGN PATENT DOCUMENTS 728 840    8/1996   European Pat. Off. .
747 483   12/1996   European Pat. Off. .
WO 89/06688 7/1989   WIPO .

OTHER PUBLICATIONS

E. Shinagawa et al., Agric. Biol. Chem. vol. 46, pp. 135–141 (1982).

E–S, Choi, et al., FEMS Microbiol. Lett. vol. 125, pp. 45–50 (1995).

*Primary Examiner*—Nashaat T. Nashed
*Attorney, Agent, or Firm*—Mark E. Waddell; Stephen M. Haracz; Bryan Cave LLP

[57] ABSTRACT

Polynucleotides encoding proteins with D-sorbitol dehydrogenase activity or which function to activate D-sorbitol dehydrogenase proteins, in vivo, vectors and recombinant organisms which contain such polynucleotides, and methods of making D-sorbitol dehydrogenase and L-sorbose.

37 Claims, 8 Drawing Sheets

PEPTIDE NO. 1   K   W   A   E   E   T   X   P

PEPTIDE NO. 3   K   S       Q   S   Y   A   P   Q   Y   A   P   Q   A   P   G   V   N   A   X   N   L
                            5' CAG TCG TAT TTC GCA GGA CC 3'
                                   AGC  C       C   G   C
                                        T               T
                            ───────── s7 : 20MER ─────────▶

PEPTIDE NO. 8   K   V       L   W   Q   H   P   L   G   T   A   R   X   N   G   P
                            3' GAG ACC GTC GTG GGG GAG CC 5'
                                        C       A   C   A
                                        A               A
                            ◀───────── s6R : 20MER ─────────

THE AMINO ACID SEQUENCE IN BOLDFACE WERE USED FOR SYNTHESIZING TWO OLIGONUCLEOTIDE SEQUENCES (S7 AND s6R) FOR PCR. ARROWS SHOW DIRECTION OF DNA SYNTHESIS. THE PRIMERS WERE DEGENERATE DNA MIXTURES HAVING BIAS FOR GLUCONOBACTER CODON USAGE.

FIG. 1

```
         10        20        30        40        50        60
ACAAATCATACTGGCGGCGCTGTAGTGACAATTCCGGCGGGTTAAAGAGAATATTTTTTT 70        80        90       100       110       120
GGTGACAGGCCACAACAAATTTTTGTTACCTCAAACACAGTTTTGTTAGAGCATTTGAAA
                                                     SD FOR ORF 2 GENE
        130       140       150       160       170       180
ACGAAGTCCGATGGACCTGAACTGAATATGGATTTACCGTCCGGAGGATTCAGTTTGGGA

190  ORF 2 200       210       220       230       240
GGCATTCGGTTATGCCAAATCTTCAAGGTAATAGGACTCTGACGGAGTGGCTGACGCTGC
           M  P  N  L  Q  G  N  R  T  L  T  E  W  L  T  L  L 250       260       270       280       290       300
TTCTCGGGGTCATCGTCCTTCTTGTGGGCCTGTTCTTCGTCATTGGGGGTGCTGACCTCG
 L  G  V  I  V  L  L  V  G  L  F  F  V  I  G  G  A  D  L  A 310       320       330       340       350       360
CGATGCTGGGCGGCTCTACCTACTATGTTCTCTGTGGCATCCTCCTGGTTGCTAGCGGCG
 M  L  G  G  S  T  Y  Y  V  L  C  G  I  L  L  V  A  S  G  V 370       380       390       400       410       420
TATTCATGCTCATGGGCCGCACGCTTGGTGCCTTCCTGTATCTGGGTGCCCTGGCCTACA
 F  M  L  M  G  R  T  L  G  A  F  L  Y  L  G  A  L  A  Y  T 430       440       450       460       470       480
CGTGGGTCTGGTCCTTCTGGGAAGTCGGTTTCAGCCCCATCGATCTTCTGCCCCGCGCTT
 W  V  W  S  F  W  E  V  G  F  S  P  I  D  L  L  P  R  A  F 490       500       510       520       530       540
TCGGCCCGACCATCCTTGGCATTCTCGTTGCCCTGACCATTCCGGTCCTGCGCCGCATGG
 G  P  T  I  L  G  I  L  V  A  L  T  I  P  V  L  R  R  M  E
   SD FOR SLDH GENE
        550       560       570  SLDH ORF    590       600
AAAGCCGTCGTACTCTCAGAGGAGCCGTCTGATGCGCCGGCCTTACCTTCTAGCAACAGC
 S  R  R  T  L  R  G  A  V   M  R  R  P  Y  L  L  A  T  A 610       620       630       640       650       660
CGCAGGACTCGCCCTTGCCTGTTCGCCGCTCATCGCTCATGCACAGTTTGCTCCCGCAGG
 A  G  L  A  L  A  C  S  P  L  I  A  H  A  Q  F  A  P  A  G
    SIGNAL SEQUENCE (24 A.A.)                ↑ N-terminus
        670       680       690       700       710       720
GGCTGGCGGCGAACCTTCCTCGTCAGTTCCTGGGCCAGGAAATGCGAGCGAGCCCACCGA
 A  G  G  E  P  S  S  S  V  P  G  P  G  N  A  S  E  P  T  E
                                IR1
        730       740       750       760       770       780
AAACTCTCCGAAAAGTCAGAGCTACTTCGCAGGACCGTCGCCCTATGCCCCGCAGGCTCC
 N  S  P  K  S  Q  S  Y  F  A  G  P  S  P  Y  A  P  Q  A  P
              PEPTIDE NO. 3 ------------------------------
        790       800       810       820       830       840
TGGCGTAAACGCAGCCAACCTGCCGGACATTGAGTCAATCGATCCCTCGCAGGTCCCGGC
 G  V  N  A  A  N  L  P  D  I  E  S  I  D  P  S  Q  V  P  A
---------
        850       860       870       880       890       900
CATGGCTCCGCAGCAGAGTGCCAATCCGGCACGTGGAGACTGGGTTGCTTACGGACGTGA
 M  A  P  Q  Q  S  A  N  P  A  R  G  D  W  V  A  Y  G  R  D
```

FIG. 3A

```
     910        920        930        940        950        960
CGATCATCAGACGCGATACTCTCCGCTTTCGGAAATCACGCCTGAGAACGCAAGCAAGCT
 D  H  Q  T  R  Y  S  P  L  S  E  I  T  P  E  N  A  S  K  L 970        980        990       1000       1010       1020
CAAGGTCGCTTTCGTCTACCACACGGGGAGTTATCCGCGTCCGGGACAGGTGAACAAATG
 K  V  A  F  V  Y  H  T  G  S  Y  P  R  P  G  Q  V  N  K  W
                                                PEPTIDE NO. 1
    1030       1040       1050       1060       1070       1080
GGCCGCCGAAACCACGCCGATCAAGGTTGGTGACGGTCTCTACACATGTTCCGCCATGAA
 A  A  E  T  T  P  I  K  V  G  D  G  L  Y  T  C  S  A  M  N 1090       1100       1110       1120       1130       1140
CGACATCATCAAGCTGGATCCGGCTACGGGTAAGCAGATCTGGCGTCGGAACGTGGATGT
 D  I  I  K  L  D  P  A  T  G  K  Q  I  W  R  R  N  V  D  V 1150       1160       1170       1180       1190       1200
CAAATACCACTCCATTCCCTATACCGCTGCCTGTAAGGGTGTGACGTATTTCACGTCCTC
 K  Y  H  S  I  P  Y  T  A  A  C  K  G  V  T  Y  F  T  S  S 1210       1220       1230       1240       1250       1260
CGTGGTGCCGGAAGGCCAGCCCTGCCACAATCGCCTTATCGAAGGCACGCTGGATATGCG
 V  V  P  E  G  Q  P  C  H  N  R  L  I  E  G  T  L  D  M  R 1270       1280       1290       1300       1310       1320
TCTGATTGCGGTTGACGCGGAGACAGGGGATTTCTGCCCTAATTTCGGTCATGGTGGTCA
 L  I  A  V  D  A  E  T  G  D  F  C  P  N  F  G  H  G  G  Q 1330       1340       1350       1360       1370       1380
GGTCAACCTGATGCAGGGTCTGGGTGAGTCTGTTCCGGGCTTCGTCTCCATGACGGCACC
 V  N  L  M  Q  G  L  G  E  S  V  P  G  F  V  S  M  T  A  P 1390       1400       1410       1420       1430       1440
TCCACCGGTCATCAACGGCGTCGTGGTTGTAAACCACGAAGTGCTCGACGGTCAGCGCCG
 P  P  V  I  N  G  V  V  V  V  N  H  E  V  L  D  G  Q  R  R 1450       1460       1470       1480       1490       1500
CTGGGCTCCGTCCGGTGTGATCCGTGGTTACGATGCTGAAAGTGGCAAATTCGTATGGGC
 W  A  P  S  G  V  I  R  G  Y  D  A  E  S  G  K  F  V  W  A 1510       1520       1530       1540       1550       1560
CTGGGACGTCAACAATTCCGGACGATCACAGCCAGCCTACCGGGTAACCGTCATTACAGC
 W  D  V  N  N  S  G  R  S  Q  P  A  Y  R  V  T  V  I  T  A 1570       1580       1590       1600       1610       1620
CGTGGAACGCCGAATTCCTGGGCTACCTGACAGGCGACAACGAGGAGGGTCTCGTTTACG
 V  E  R  R  I  P  G  L  P  D  R  R  Q  R  G  G  S  R  L  R 1630       1640       1650       1660       1670       1680
TCCCGACAGGAACTCTGCTGCTGACTATTACAGCGCCCTGCGTAGTGATGCTGAAAACAA
 P  D  R  N  S  A  A  D  Y  Y  S  A  L  R  S  D  A  E  N  K 1690       1700       1710       1720       1730       1740
GGTGTCCTCCGCTGTTGTCGCCATTGACGTCAAGACGGGTTCTCCGCGCTGGGTCTTCCA
 V  S  S  A  V  V  A  I  D  V  K  T  G  S  P  R  W  V  F  Q 1750       1760       1770       1780       1790       1800
GACGGCTCATAAGGACGTCTGGGATTATGACATCGGTTCACAGGCGACCCTGATGGATAT
 T  A  H  K  D  V  W  D  Y  D  I  G  S  Q  A  T  L  M  D  M
```

FIG. 3B

```
        1810      1820      1830      1840      1850      1860
GCCTGGCCCGGATGGCCAGACGGTTCCTGCTCTCATCATGCCGACCAAGCGTGGCCAGAC
  P  G  P  D  G  Q  T  V  P  A  L  I  M  P  T  K  R  G  Q  T 1870      1880      1890      1900      1910      1920
GTTCGTGCTTGACCGTCGTACCGGCAAGCCAATTCTGCCGGTTGAAGAACGCCCAGCTCC
  F  V  L  D  R  R  T  G  K  P  I  L  P  V  E  E  R  P  A  P 1930      1940      1950      1960      1970      1980
GTCCCCTGGTGTTATTCCGGGTGACCCGCGTTCTCCGACGCAGCCATGGTCCGTCGGGAT
  S  P  G  V  I  P  G  D  P  R  S  P  T  Q  P  W  S  V  G  M 1990      2000      2010      2020      2030      2040
GCCGGCCCTTCGCGTGCCGGATCTGAAAGAGACAGACATGTGGGGTATGTCCCCCATCGA
  P  A  L  R  V  P  D  L  K  E  T  D  M  W  G  M  S  P  I  D 2050      2060      2070      2080      2090      2100
TCAGCTCTTCTGCCGTATCAAGTTCCGCCGTGCGAACTATGTGGGTGAGTTCACACCACC
  Q  L  F  C  R  I  K  F  R  R  A  N  Y  V  G  E  F  T  P  P 2110      2120      2130      2140      2150      2160
GAGCGTTGACAAGCCGTGGATTGAATATCCGGGCTATAACGGTGGCAGTGACTGGGGCTC
  S  V  D  K  P  W  I  E  Y  P  G  Y  N  G  G  S  D  W  G  S 2170      2180      2190      2200      2210      2220
CATGTCCTATGATCCGCAGTCCGGCATCCTGATTGCGAACTGGAACATCACACCGATGTA
  M  S  Y  D  P  Q  S  G  I  L  I  A  N  W  N  I  T  P  M  Y 2230      2240      2250      2260      2270      2280
CGACCAGCTCGTAACCCGCAAGAAGGCAGACTCCCTCGGCCTGATGCCGATCGATGACCC
  D  Q  L  V  T  R  K  K  A  D  S  L  G  L  M  P  I  D  D  P 2290      2300      2310      2320      2330      2340
CAACTTCAAGCCAGGTGGCGGTGGTGCCGAAGGTAACGGCGCCATGGACGGAACGCCTTA
  N  F  K  P  G  G  G  G  A  E  G  N  G  A  M  D  G  T  P  Y 2350      2360      2370      2380      2390      2400
CGGTATCGTCGTGACACCGTTCTGGGATCAGTACACGGGCATGATGTGCAACCGTCCGCC
  G  I  V  V  T  P  F  W  D  Q  Y  T  G  M  M  C  N  R  P  P 2410      2420      2430      2440      2450      2460
CTACGGTATGATCACAGCCATCGACATGAAGCACGGCCAGAAGGTTCTGTGGCAGCATCC
  Y  G  M  I  T  A  I  D  M  K  H  G  Q  K  V  L  W  Q  H  P
                                          PEPTIDE NO. 8
        2470      2480      2490      2500      2510      2520
GCTCGGAACGGCTCGCGCCAACGGTCCATGGGGTCTGCCAACAGGTCTGCCATGGGAAAT
  L  G  T  A  R  A  N  G  P  W  G  L  P  T  G  L  P  W  E  I 2530      2540      2550      2560      2570      2580
CGGCACTCCGAACAATGGTGGTTCGGTTGTGACCGGTGGCGGTCTGATCTTCATCGGTGC
  G  T  P  N  N  G  G  S  V  V  T  G  G  G  L  I  F  I  G  A 2590      2600      2610      2620      2630      2640
GGCAACGGATAACCAGATCCGCGCGATTGATGAACACACTGGCAAGGTTGTCTGGAGCGC
  A  T  D  N  Q  I  R  A  I  D  E  H  T  G  K  V  V  W  S  A 2650      2660      2670      2680      2690      2700
AGTCCTCCCCGGCGGCGGTCAGGCCAATCCGATGACGTATGAAGCCAATGGTCACCAGTA
  V  L  P  G  G  G  Q  A  N  P  M  T  Y  E  A  N  G  H  Q  Y
```

FIG. 3C

```
        2710      2720      2730      2740      2750      2760
CGTTGCCATCATGGCTGGCGGTCATCACTTCATGATGACGCCAGTGTCTGACCAGCTTGT
 V  A  I  M  A  G  G  H  H  F  M  M  T  P  V  S  D  Q  L  V 2770      2780      2790      2800      2810      2820
GGTTTACGCACTGCCGGATGCCATCAAGCAGTAATTAAGTCCTGTGGCGGATGTGTCATG
 V  Y  A  L  P  D  A  I  K  Q  *                    ─────────
                                                         IR2

2830      2840      2850      2860      2870      2880
CATATCCGCCACACTCCATCGTCAGAAGGAGACTTTCGTGCTAGCCATGCAGGGAAGTCT
───────────   ──────────────────────────────────→ ←──────────
                                                  IR2'

2890      2900      2910      2920      2930      2940
CCTTTTGACGTTTTTGGCTCTTTCCAGCGAGCGGGCAGTCTGAAACGGGGCTTCGTCTGG
──────────

2950      2960      2970      2980      2990      3000
CTCGTACTTTCAGAATGGCTCGTCGCACCCTCATGACTGCCCACTCCCCCGTTATCTTGC 3010      3020      3030      3040      3050      3060
AGGTTCTGCCAGCCCTCAGCACGGGCGGCCTGGAGCGGGGAGCTATTGAAATTGCGGCTG 3070      3080      3090      3100      3110      3120
CCATCACACAGGCTGGTGGCAAGGCCATTGTCGCTTCGAAGACGGGTCCTCTTCTTGTGC 3130      3140      3150      3160      3170      3180
AACTCCGCCACGTCGGAGCAGTGCATGTGCCGCTGGATCTCAAATCGAAATCGCCGTTTT 3190      3200      3210      3220      3230      3240
CTGTTCGGCGCCGTGCCCGTGAACTCCAGAAACTGATCCGGGAGCAGCAGGTTGATCTGG 3250      3260      3270      3280      3290      3300
TTCACGCCCGGTCCCGTATTCCGGCATGGGCCGCCTGGCTCGCCTGCCGCCGCGAGAACA 3310      3320      3330      3340      3350      3360
TTCCTTTCGTGACAACGTGGCATGGCGTCCACGAGGCTGGCTGGTGGGGCAAGAAATTCT 3370      3380      3390      3400      3410      3420
ACAATTCGGTGCTGGCCCGGGGTGCAAGGGTCATCGCAATTTCGCACTACATTTCCGGGC 3430      3440      3450      3460      3470      3480
GTCTTTCAGGGCAGTACGGCGTTCAGGCAGATCGTCTTCGAACCATTCCGCGTGGTGCCG
3481
A          ────────→ : IR1 AND IR2 (OR 2') ARE INVERTED
                      REPEATS AS POSSIBLE TRANSCRIPTION
                      TERMINATORS FOR ORF2 AND SLDH II GENES,
                      RESPECTIVELY.
```

FIG. 3D

D-SORBITOL DEHYDROGENASE GENE

BACKGROUND OF THE INVENTION

The present invention relates to a novel DNA coding for D-sorbitol dehydrogenase of a microorganism belonging to acetic acid bacteria including the genus Gluconobacter and the genus Acetobacter, an expression vector containing the said DNA, and recombinant organisms containing the said expression vector. Furthermore, the present invention relates to a process for producing recombinant D-sorbitol dehydrogenase protein and a process for producing L-sorbose by utilizing the said recombinant enzymes or recombinant organisms containing the said expression vector.

L-Sorbose is an important intermediate in the actual industrial process of vitamin C production, which is mainly practiced by Reichstein method (Helvetica Chimica Acta, 17: 311, 1934). In the process, the only microbial conversion is the L-sorbose production from D-sorbitol by Gluconobacter or Acetobacter strains. The conversion is considered to be carried out by NAD/NADP independent D-sorbitol dehydrogenase (SLDH). L-Sorbose is also a well known substrate in the art for microbiologically producing 2-keto-L-gulonic acid, which is a useful intermediate in the production of vitamin C.

It is known that there are NAD/NADP-independent D-sorbitol dehydrogenases which catalyze the oxidation of D-sorbitol to L-sorbose. One such D-sorbitol dehydrogenase was isolated and characterized from *Gluconobacter suboxydans* var α IFO 3254 (E. Shinagawa et al., Agric Biol. Chem., 46: 135–141, 1982), and found to consist of three subunits with the molecular weight of 63 kDa, 51 kDa, and 17 kDa; the largest subunit is dehydrogenase containing FAD as a cofactor, the second one is cytochrome c and the smallest one is a protein with unknown function; and shows its optimal pH at 4.5. Such SLDH was also purified and characterized from *G. suboxydans* ATCC 621 (KCTC 2111) (E-S Choi et al., FEMS Microbiol. Lett. 125:45–50, 1995) and found to consist of three subunits with the molecular weight of 75 kDa, 50 kDa, and 14 kDa; the large subunit is dehydrogenase containing pyrroloquinoline quinone (PQQ) as a cofactor, the second one is cytochrome c and the small one is a protein with unknown function. The inventors also purified and characterized the NAD/NADP-independent SLDH from *G. suboxydans* IFO 3255 (T. Hoshino et al., EP 728840); the SLDH consists of one kind of subunit with the molecular weight of 79.0 +/−0.5 kDa and shows its optimal pH at 6 to 7 and shows dehydrogenase activity on mannitol and glycerol as well as on D-sorbitol.

Although several SLDHs have been purified, their genes have not been cloned yet. It is useful to clone the SLDH gene for efficient production of the SLDH enzyme and for constructing recombinant organism having enhanced SLDH activity to improve the production yield of L-sorbose. It is also useful to introduce the said SLDH gene into desired organisms, for example, Gluconobacter converting L-sorbose to 2-keto-L-gulonic acid for constructing recombinant microorganisms which directly produce 2-keto-L-gulonic acid from D-sorbitol.

SUMMARY OF THE INVENTION

The present invention provides a polynucleotide (i.e. nucleotide sequence or gene) coding for D-sorbitol dehydrogenase protein (SLDH) originating from a microorganism belonging to acetic acid bacteria including the genus Gluconobacter and the genus Acetobacter; a DNA molecule comprising said nucleotide sequence as well as a combination of the said DNA with a DNA comprising a nucleotide sequence of a protein functional in activating the said SLDH in vivo, expression vectors carrying the DNA comprising SLDH nucleotide sequence or the said combination of the DNAs; recombinant organisms carrying the expression vectors; a process for producing the recombinant SLDH; and a process for producing L-sorbose by utilizing the recombinant SLDH or the recombinant organisms.

Therefore this invention is directed to a polynucleotide comprising a nucleotide sequence which encodes a protein having the amino acid sequence from position 1 to position 716 of SEQ ID NO: 2, or a protein derived from that protein by substitution, deletion, insertion or addition of one or more amino acids in the amino acid sequence of positions 1–716 of SEQ ID NO. 2, which protein has D-sorbitol dehydrogenase (SLDH) activity, i.e. converts D-sorbitol to L-sorbose. Such a polynucleotide preferably encodes a protein derived from an acetic acid bacterium, in particular an acetic acid bacterium belonging to the genus Gluconobacter or the genus Acetobacter. This invention is also directed to an expression vector comprising such a polynucleotide, especially one which is functional in a microorganism belonging to the genus Gluconobacter or the genus Acetobacter or which is an *E. coli*. This invention also includes a recombinant organism comprising such an expression vector, especially one which has the polynucleotide on its chromosomal DNA, and preferably one which is a Gluconobacter, Acetobacter, or an *E. coli*.

This invention is also directed to a polynucleotide as described above consisting of a polynucleotide comprising a nucleotide sequence from position 644 to position 2791 of SEQ ID NO: 1, or a polynucleotide comprising a nucleotide sequence from position 572 to position 2791 of SEQ ID NO. 1, or polynucleotides capable of hybridizing to the above polynucleotides, and which encode proteins having D-sorbitol dehydrogenase protein activity.

This invention includes a polynucleotide which comprises a nucleotide sequence from position 192 to position 569 of SEQ ID NO: 1 and a polynucleotide which is capable of hybridizing to this polynucleotide and which encodes a protein which functions to activate a D-sorbitol dehydrogenase protein encoded by a polynucleotide of this invention (SLDH) in vivo, for example by helping to form and stabilize the SLDH when both proteins are present in an in vivo environment. This invention is also directed to an expression vector comprising such a polynucleotide, especially one which is functional in a microorganism belonging to the genus Gluconobacter or the genus Acetobacter or which is an *E. coli*. This invention also includes a recombinant organism comprising such an expression vector, especially one which has the polynucleotide on its chromosomal DNA, and preferably one which is a Gluconobacter, Acetobacter, or an *E. coli*.

Also part of this invention is a polynucleotide comprising a nucleotide sequence which encodes a polypeptide having the amino acid sequence of SEQ ID NO. 3 or a protein derived from the polypeptide by substitution, deletion, insertion or addition of one or more amino acids in the amino acid sequence of SEQ ID NO. 3, which protein functions to activate a D-sorbitol dehydrogenase protein of this invention (SLDH), in vivo (by this is meant that when the protein and SLDH are together in vivo, for example in a microorganism, the protein functions to form and stabilize the active SLDH which catalyzes the conversion of D-sorbitol to L-sorbose).

Another polynucleotide of this invention comprises the nucleotide sequence of SEQ ID NO. 1.

Any of the individual polynucleotides described above may be found in vectors of this invention, especially expression vectors. Similarly, any of the polynucleotides described above may be found in a recombinant organism (i.e. host cell) of this invention, either integrated into the host DNA, or on a vector such as an expression vector of this invention. Preferred vectors are those which function in the preferred recombinant organisms which are members of the genus Acetobacter, the genus Gluconobacter, or are E. colis.

Also part of this invention are polynucleotides which combine the nucleotide sequences of other polynucleotides of this invention. These sequences may be in tandem (i.e. end to end), or may be separated by other coding or noncoding sequences.

One such polynucleotide comprises a nucleotide sequence which encodes a protein having the amino acid sequence from position 1 to position 716 of SEQ ID NO: 2 or a protein derived from that protein by substitution, deletion, insertion or addition of one or more amino acids in the amino acid sequence (i.e. position 1 to 716 of SEQ ID NO. 2) which protein has D-sorbitol dehydrogenase activity and a nucleotide sequence from position 192 to position 569 of SEQ ID NO: 1 or a polynucleotide which is capable of hybridizing to this polynucleotide and which encodes a protein which functions to activate a D-sorbitol dehydrogenase protein encoded by a polynucleotide of this invention in vivo.

Another such polynucleotide comprises a nucleotide sequence which encodes a protein having the amino acid sequence from position 1 to position 716 of SEQ ID NO: 2, or a protein derived from that protein by substitution, deletion, insertion or addition of one or more amino acids in the amino acid sequence (i.e.position 1–716 of SEQ ID NO. 2) which protein has D-sorbitol dehydrogenase activity; and a nucleotide sequence which encodes a polypeptide having the amino acid sequence of SEQ ID NO. 3; or a protein derived from that protein by substitution, deletion, insertion or addition of one or more amino acids in the amino acid sequence (i.e. SEQ ID NO. 3), which protein functions to activate a D-sorbitol dehydrogenase protein encoded by a polynucleotide of this invention in vivo.

Another such polynucleotide comprises a nucleotide sequence from position 644 to position 2791 of SEQ ID NO: 1 or a nucleotide sequence from position 572 to position 2791 of SEQ ID NO. 1, or polynucleotides capable of hybridizing to the above nucleotide sequences and encoding a D-sorbitol dehydrogenase protein of this invention; and a nucleotide sequence from position 192 to position 569 of SEQ ID NO: 1 or a polynucleotide which is capable of hybridizing to that polynucleotide and which encodes a protein which functions to activate the D-sorbitol dehydrogenase protein encoded by a polynucleotide of this invention, in vivo.

Yet another polynucleotide comprises a nucleotide sequence from position 644 to position 2791 of SEQ ID NO: 1 or a nucleotide sequence from position 572 to position 2791 of SEQ ID NO. 1, or polynucleotides capable of hybridyzing to these nucleotide sequences and which encode a D-sorbitol dehydrogenase protein of this invention, and a polynucleotide comprising a nucleotide sequence which encodes a polypeptide having the amino acid sequence of SEQ ID NO. 3 or a protein derived from that protein by substitution, deletion, insertion or addition of one or more amino acids in the amino acid sequence (i.e. SEQ ID NO. 3) which protein functions to activate a D-sorbitol dehydrogenase protein encoded by a polynucleotide of this invention, in vivo.

This invention includes a polynucleotide which comprises a nucleotide sequence from position 572 to position 2791 of SEQ ID NO. 1 and a polynucleotide comprising a nucleotide sequence from position 192 to position 569 of SEQ ID NO. 1.

The polynucleotides of this invention are preferably obtained from Gluconobacter or Acetobacter organisms as noted above.

This invention is also directed to recombinant organisms which are host cells for the polynucleotides of this invention, and preferably are capable of expressing these polynucleotides. The polynucleotide may be on a vector of any type or integrated into the recombinant organism's own DNA. In the case of recombinant organisms which contain more than one polynucleotide of this invention, the polynucleotides may be on a single vector, may be on separate vectors, or may be integrated into the DNA of the recombinant organism. Within one host cell containing multiple polynucleotides, one or more polynucleotides may be integrated into the host DNA while one or more are on vectors. Thus this invention contemplates a vector, especially an expression vector, containing any individual polynucleotide of this invention, and also a recombinant organism containing any individual polynucleotide of this invention. It is preferred that the recombinant organism contain two polynucleotides, one of which encodes a protein of this invention which has D-sorbitol dehydrogenase protein activity, and the other of which encodes a protein of this invention which functions to activate a D-sorbitol dehydrogenase protein encoded by a polynucleotide of this invention in vivo.

Preferred vectors are those vectors which are designed to function in microorganisms which are members of the genera Gluconobacter or Acetobacter, or in E. coli. Similarly, preferred recombinant organisms as host cells of this invention are members of the genera Gluconobacter or Acetobacter, or are E. coli Thus part of this invention is recombinant organism which contains both a polynucleotide comprising a nucleotide sequence which encodes a protein having the amino acid sequence from position 1 to position 716 of SEQ ID NO: 2 or a protein derived from that protein by substitution, deletion, insertion or addition of one or more amino acids in the amino acid sequence (i.e. 1–716 of SEQ ID NO.2) which protein has D-sorbitol dehydrogenase activity, and contains a polynucleotide comprises a nucleotide sequence from position 192 to position 569 of SEQ ID NO: 1 or a polynucleotide which is capable of hybridizing to that polynucleotide and which encodes a protein which functions to activate a D-sorbitol dehydrogenase protein encoded by a polynucleotide of this invention in vivo.

Also part of this invention is a recombinant organism which contains both a polynucleotide comprising a nucleotide sequence which encodes a protein having the amino acid sequence from position 1 to position 716 of SEQ ID NO: 2 or a protein derived from that protein by substitution, deletion, insertion or addition of one or more amino acids in the amino acid sequence (i.e. 1–716 of SEQ ID NO. 2), which protein has D-sorbitol dehydrogenase activity; and a polynucleotide comprising a nucleotide sequence which encodes a polypeptide having the amino acid sequence of SEQ ID NO. 3 or a protein derived from that protein by substitution, deletion, insertion or addition of one or more amino acids in SEQ ID NO. 3 which protein functions to activate a D-sorbitol dehydrogenase protein encoded by a polynucleotide of this invention in vivo.

Another recombinant organism of this invention contains both a polynucleotide comprising a nucleotide sequence from position 644 to position 2791 of SEQ ID NO: 1 or a polynucleotide capable of hybridizing to this polynucleotide and encoding a protein having D-sorbitol dehydrogenase activity; or a polynucleotide comprising a nucleotide sequence from position 572 to position 2791 of SEQ ID NO. 1 or a polynucleotide capable of hybridizing to this polynucleotide and encodes a protein having D-sorbitol dehydrogenase activity; and a polynucleotide comprising a nucleotide sequence from position 192 to position 569 of SEQ ID NO: 1 or a polynucleotide which is capable of hybridizing to this polynucleotide and encoding a protein which functions to activate a D-sorbitol dehydrogenase protein encoded by a polynucleotide of this invention in vivo.

Yet another recombinant organism of this invention contains both a polynucleotide comprising a nucleotide sequence from position 644 to position 2791 of SEQ ID NO: 1 or a polynucleotide capable of hybridizing to this polynucleotide and encoding a protein having D-sorbitol dehydrogenase activity; or a polynucleotide comprising a nucleotide sequence from position 572 to position 2791 of SEQ ID NO. 1 or a polynucleotide capable of hybridizing to this polynucleotide and encoding a protein having D-sorbitol dehydrogenase activity, and a polynucleotide comprising a nucleotide sequence which encodes a polypeptide having the amino acid sequence of SEQ ID NO. 3 or a protein derived from this protein by substitution, deletion, insertion or addition of one or more amino acids in SEQ ID NO. 3, which protein functions to activate a D-sorbitol dehydrogenase protein encoded by a polynucleotide of this invention in vivo.

Another recombinant organism of this invention contains both a polynucleotide comprising a nucleotide sequence from position 572 to position 2791 of SEQ ID NO. 1 and a polynucleotide comprising a nucleotide sequence from position 192 to position 569 of SEQ ID NO. 1. A preferred such recombinant organism has these polynucleotides in its chromosomal DNA. It is also preferable that the recombinant organism belongs to the genus Gluconobacter, the genus Acetobacter, or is an *E. coli*.

Also part of this invention are expression vectors containing one or more of the polynucleotides of this invention. Expression vectors are well known in the art and are described below. Preferred expression vectors are designed to function in Gluconobacter or Acetobacter organisms, or in *E. coli*. An expression vector of this invention may contain more than one polynucleotide of this invention which may be in tandem (end-to-end) or may be separated within the vector by other DNA sequences. It is preferred that the vector contain two polynucleotides, one of which encodes a protein of this invention which has D-sorbitol dehydrogenase activity, and the other of which encodes a protein of this invention which functions to activate a D-sorbitol dehydrogenase protein encoded by a polynucleotide of this invention in vivo.

A particular expression vector of this invention contains a polynucleotide comprising a nucleotide sequence which encodes a protein having the amino acid sequence from position 1 to position 716 of SEQ ID NO: 2 or a protein derived from that protein by substitution, deletion, insertion or addition of one or more amino acids in the amino acid sequence (i.e. 1–716 of SEQ ID NO. 2) which protein has D-sorbitol dehydrogenase activity, and a polynucleotide comprising a nucleotide sequence from position 192 to position 569 of SEQ ID NO: 1 or a polynucleotide which is capable of hybridizing to that polynucleotide and which encodes a protein which functions to activate a D-sorbitol dehydrogenase protein encoded by a polynucleotide of this invention in vivo.

Another expression vector of this invention contains a polynucleotide comprising a nucleotide sequence which encodes a protein having the amino acid sequence from position 1 to position 716 of SEQ ID NO: 2 or a protein derived from that protein by substitution, deletion, insertion or addition of one or more amino acids in the amino acid sequence (i.e. 1–716 of SEQ ID NO. 2) which protein has D-sorbitol dehydrogenase activity, and a polynucleotide comprising a 25 nucleotide sequence which encodes a polypeptide having the amino acid sequence of SEQ ID NO. 3 or a protein derived from that protein by substitution, deletion, insertion or addition of one or more amino acids in SEQ ID NO. 3 which protein functions to activate a D-sorbitol dehydrogenase protein encoded by a polynucleotide of this invention in vivo.

Yet another expression vector of this invention contains a polynucleotide comprising a nucleotide sequence from position 644 to position 2791 of SEQ ID NO: 1 or a polynucleotide comprising a nucleotide sequence from position 572 to position 2791 of SEQ ID NO. 1 or polynucleotides capable of hybridizing to the above polynucleotides and which encode proteins having D-sorbitol dehydrogenase activity, and a polynucleotide comprising a nucleotide sequence from position 192 to position 569 of SEQ ID NO: 1 or a polynucleotide which is capable of hybridizing to that polynucleotide and which encodes a protein which functions to activate a D-sorbitol dehydrogenase protein encoded by a polynucleotide of this invention in vivo.

Yet another expression vector of this invention contains a polynucleotide comprising a nucleotide sequence from position 644 to position 2791 of SEQ ID NO: 1 or a polynucleotide comprising a nucleotide sequence from position 572 to position 2791 of SEQ ID NO. 1 or polynucleotides capable of hybridizing to the above polynucleotides and which encode proteins having D-sorbitol dehydrogenase activity, and a polynucleotide comprising a nucleotide sequence which encodes a polypeptide having the amino acid sequence of SEQ ID NO. 3 or a protein derived from that protein by substitution, deletion, insertion or addition of one or more amino acids in SEQ ID NO. 3 which protein functions to activate a D-sorbitol dehydrogenase protein encoded by a polynucleotide of this invention in vivo.

This invention also includes an expression vector which contains a polynucleotide comprising a nucleotide sequence from position 572 to position 2791 of SEQ ID NO. 1 and a polynucleotide comprising a nucleotide sequence from position 192 to position 569 of SEQ ID NO. 1.

Another particular expression vector of this invention contains a polynucleotide comprising a nucleotide sequence which encodes a protein having the amino acid sequence from position 1 to position 716 of SEQ ID NO. 2, or a protein derived from that protein substitution, deletion, insertion or addition of one or more amino acids in the amino acid sequence of positions 1–716 of SEQ ID NO. 2, which protein has D-sorbitol dehydrogenase activity. A preferred such vector is functional in a microorganism belonging to the genus Gluconobacter, the genus Acetobacter, or *E. coli*.

Also part of this invention is a process for producing recombinant D-sorbitol dehydrogenase protein encoded by a polynucleotide of this invention by cultivating any of the recombinant organisms of this invention as described specifically above, especially the recombinant organisms which contain two polynucleotides of this invention one encoding recombinant D-sorbitol dehydrogenase and the other encoding a protein which functions to activate the D-sorbitol dehydrogenase protein encoded by a polynucleotide of this invention(in vivo), in an appropriate medium and recovering the said recombinant D-sorbitol from the culture. Accordingly, part of this invention is a recombinant D-sorbitol dehydrogenase protein produced by this process. A preferred such recombinant D-sorbitol dehydrogenase is immobilized on a solid carrier for solid phase enzymatic reaction.

Another process of this invention is a process for producing L-sorbose which comprises converting D-sorbitol into L-sorbose with the aid of the recombinant D-sorbitol dehydrogenase protein encoded by a polynucleotide of this invention.

Yet another process of this invention is a process for producing L-sorbose which comprises converting D-sorbitol into L-sorbose by fermentation of any of the recombinant organisms of this invention as described specifically above especially the recombinant organisms which contain two polynucleotides of this invention one encoding recombinant D-sorbitol dehydrogenase protein and the other encoding a protein which functions to activate the D-sorbitol dehydrogenase protein encoded by a polynucleotide of this invention (in vivo), in an appropriate medium.

A BRIEF DESCRIPTION OF THE DRAWINGS

FIG. 1 illustrates the partial amino acid sequences of SLDH polypeptide and oligonucleotides. The amino acid sequences in boldface in the figure were used for synthesizing two oligonucleotide sequences (S7 and S6R) for PCR. Arrow shows direction of DNA synthesis. All primers were degenerate DNA mixtures having bias for Gluconobacter codon usage. Peptide No. 1 is SEQ ID NO. 4; Peptide No. 3 is SEQ ID NO. 5; Peptide No. 8 is SEQ ID NO. 6.

FIGS. 3a–3d illustrates the nucleotide sequence encoding SLDH and ORF2 with upstream and downstream sequences (SEQ ID NO. 1) and illustrates deduced amino acid sequences of SLDH and ORF2 (SEQ ID NO. 2, SEQ ID NO. 3). FIG. 3 also illustrates putative ribosome-binding sites (SD sequences) of SLDH and ORF2 genes and the possible transcription terminator sequences.

DETAILED DESCRIPTION OF THE INVENTION

Figure 2:
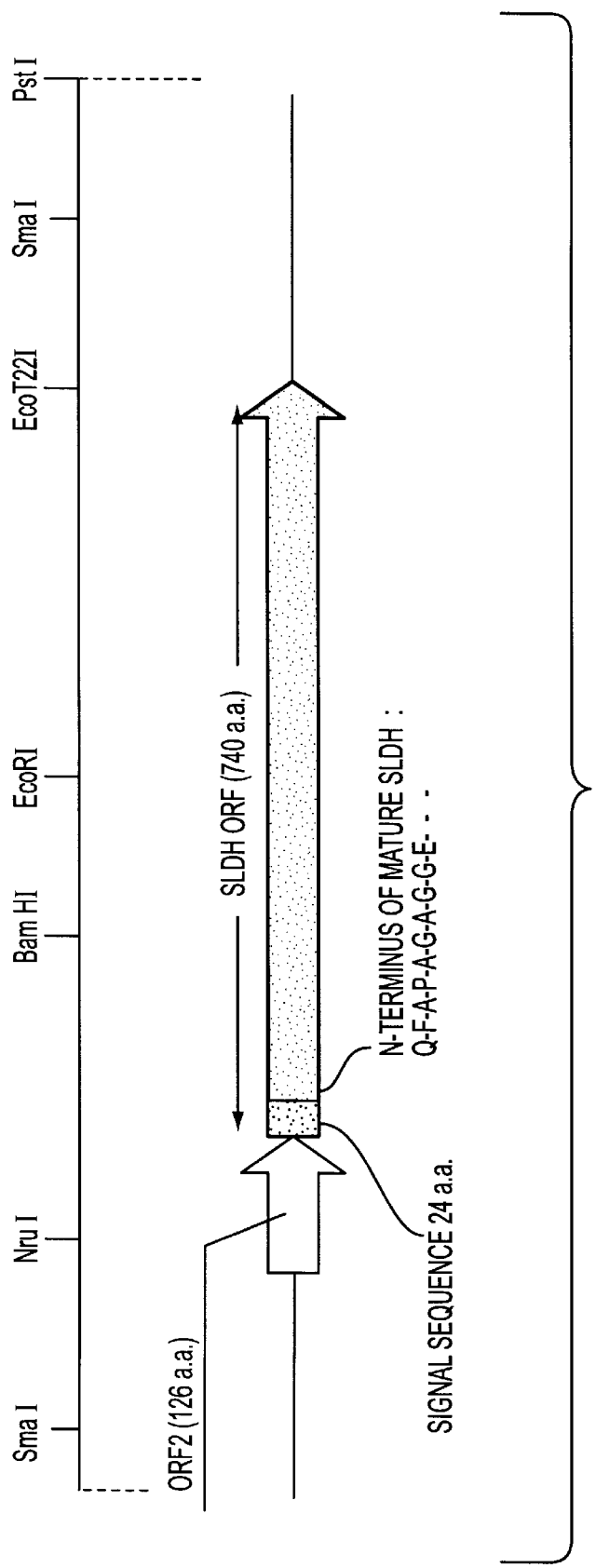
FIG. 2 illustrates a restriction map of the SLDH gene cloned in the present invention and the genetic structure of the DNA region encoding SLDH and ORF2.

The present invention is also directed to functional derivatives of the present case. Such functional derivatives are defined on the basis of the amino acid sequences of the present invention by addition, insertion, deletion and/or substitution of one or more amino acid residues of such sequences wherein such derivatives still have SLDH activity measured by an assay known in the art or specifically described herein. Such functional derivatives can be made either by chemical peptide synthesis known in the art or by recombinant means on the basis of the DNA sequences as disclosed herein by methods known in the state of the art and disclosed e.g. by Sambrook et al. (Molecular Cloning, Cold Spring Harbour Laboratory Press, New York, USA, second edition 1989). Amino acid exchanges in proteins and peptides which do not generally alter the activity of such molecules are known in the state of the art and are described, for example, by H. Neurath and R. L. Hill in The Proteins (Academic Press, New York, 1979, see especially Figure 6, page 14). The most commonly occurring exchanges are: Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly as well as these in reverse.

Furthermore the present invention is directed to polynucleotides (DNA sequences) encoding polypeptides with SLDH activity and polypeptides functional in activating the said SLDH in vivo as disclosed e.g. in the sequence list as SEQ ID NO:2 and NO:3 as well as their complementary strands, or those which include these sequences, DNA sequences which hybridize under standard conditions with such sequences or fragments thereof and DNA sequences, which because of the degeneracy of the genetic code, do not hybridize under standard conditions with such sequences but which code for polypeptides having exactly the same amino acid sequence.

Standard conditions for hybridization mean in this context the conditions which are generally used by a man skilled in the art to detect specific hybridization signals and which are described, e. g. by Molecular Cloning, Cold Spring Harbour Laboratory Press, New York, USA, second edition 1989, or preferably so called stringent hybridization and stringent washing conditions a man skilled in the art is familiar with and which are described, e. g. in Sambrook et al. (s. a.).

The inventors have isolated SLDH gene together with a gene functional in developing SLDH activity in vivo by DNA recombinant techniques and determined the nucleotide sequences.

The present invention provides DNA sequences encoding Gluconobacter SLDH and a gene functional in developing SLDH activity in vivo herein after referred to as ORF2 gene, expression vectors containing the said DNA for SLDH and recombinant organisms acting as host cells carrying the said expression vectors.

Briefly, the SLDH and/or ORF2 gene(s), the DNA molecule containing the said gene(s), the recombinant expression vector and the recombinant organism utilized in the present invention can be obtained by the following steps:

(1) Isolating chromosomal DNA from the microorganisms which can provide SLDH activity that converts D-sorbitol to L-sorbose and constructing the gene library with the chromosomal DNA in an appropriate host cell, e. g. *E. coli.*

(2) Cloning SLDH and/or ORF2 gene(s) from a chromosomal DNA by colony-, plaque-, or Southern-hybridization, PCR (polymerase chain reaction) cloning, Western-blot analysis and the like.

(3) Determining the nucleotide sequence of the SLDH and/or ORF2 gene(s) obtained as above by conventional methods to select DNA molecule containing said SLDH and/or ORF2 gene(s) and constructing the recombinant expression vector on which SLDH and/or ORF2 gene(s) can express efficiently.

(4) Constructing recombinant organisms carrying SLDH and/or ORF2 gene(s) by an appropriate method for introducing DNA into host cell, e. g. transformation, transduction, transconjugation and/or electroporation, which host cell thereby becomes a recombinant organism of this invention.

The materials and the techniques used in the above aspect of the present invention are exemplified in details as follows:

A total chromosomal DNA can be purified by a procedure well known in the art. The aimed gene can be cloned in either plasmid or phage vectors from a total chromosomal DNA typically by either of the following illustrative methods:

(i) The partial amino acid sequences are determined from the purified proteins or peptide fragments thereof. Such whole protein or peptide fragments can be prepared by the isolation of such a whole protein or by peptidase-treatment from the gel after SDS-polyacrylamide gel electrophoresis. Thus obtained protein or fragments thereof are applied to protein sequencer such as Applied Biosystems automatic gas-phase sequencer 470A. The amino acid sequences can be utilized to design and prepare oligonucleotide probes and/or primers with DNA synthesizer such as Applied Biosystems automatic DNA sequencer 381A. The said probes can be used for isolating clones carrying the target gene from a gene library of the strain carrying the target gene with the aid of Southern-, colony- or plaque-hybridization.

(ii) Alternatively, for the purpose of selecting clones expressing target protein from the gene library, immunological methods with antibody prepared against the target protein can be applied.

(iii) The DNA fragment of the target gene can be amplified from the total chromosomal DNA by PCR method with a set of primers, i.e. two oligonucleotides synthesized according to the amino acid sequences determined as above. Then a clone carrying the target-whole gene can be isolated from the gene library constructed, e.g. in *E. coli* by Southern-, colony-, or plaque-hybridization with the PCR product obtained above as the probe.

(iv) A further alternative way of the cloning is screening of the clone complementing SLDH-deficient strain constructed by conventional mutation with chemical mutagenesis or by recombinant DNA techniques e.g. with transposon Tn5 to disrupt target gene.

DNA sequences which can be made by the polymerase chain reaction by using primers designed on the basis of the DNA sequences disclosed therein by methods known in the art are also an object of the present invention. It is understood that the DNA sequences of the present invention can also be made synthetically as described, e.g. in EP 747 483.

Above mentioned antibody can be prepared with purified SLDH protein or its peptide fragment as an antigen by such method described in Methods in Enzymology, vol. 73, p 46, 1981.

Once a clone carrying the desired gene is obtained, the nucleotide sequence of the target gene can be determined by a well known method such as dideoxy chain termination method with M13 phage (Sanger F. et al., Proc. Natl. Acad. Sci. USA, 74:5463–5467, 1977).

The desired gene expressing the D-sorbitol dehydrogenase activity of the present invention is illustrated in FIG. 2 and FIG. 3. This specific gene encodes the SLDH enzyme having 716 amino acid residues together with a signal peptide of 24 amino acid residues (SEQ ID NO. 2). The inventors found an open reading frame just upstream of the above SLDH structure gene and designated it as ORF2. This ORF2 gene encodes a protein having 126 amino acid residues (SEQ ID NO. 3), and was suggested to function in providing the desired enzymatic activity to the recombinant SLDH of the present invention, in particular when the said SLDH is expressed by a recombinant organism which is a host cell of a different genus from acetic acid bacteria. In terms of nucleotide sequences, the coding region of the SLDH gene is 572 to 2794 of SEQ ID NO:1 and includes the signal peptide (572 to 643) and the stop codon (2792 to 2794). Thus the sequence without the stop codon is 572 to 2791, and additionally without the signal sequence is 644 to 2791. The coding region of ORF2 is 192 to 572 of SEQ ID NO:1 and includes the stop codon (570 to 572). Thus the sequence without the stop codon is 192 to 569.

To express the desired gene/nucleotide sequence isolated from acetic acid bacteria including genus Gluconobacter and genus Acetobacter efficiently, various promoters can be used; for example, the original promoter of the gene, promoters of antibiotic resistance genes such as kanamycin resistant gene of Tn5 (D. E. Berg, and C. M. Berg. 1983. Bio/Technology 1:417–435), ampicillin resistant gene of pBR322, and β-galactosidase of *E. coli* (lac), trp-, tac-, trc-promoter, promoters of lambda phage and any promoters which can be functional in a host organism. For this purpose, the host organism can be selected from microorganisms including bacteria such as *Escherichia coli, Pseudomonas putida, Acetobacter xylinum, Acetobacter pasteurianus, Acetobacter aceti, Acetobacter hansenii*, and *Gluconobacter albidus, Gluconobacter capsulatus, Gluconobacter cerinus, Gluconobacter dioxyacetonicus, Gluconobacter gluconicus, Gluconobacter intdustrius, Gluconobacter melanogenus, Gluconobacter nonxygluconicus, Gluconobacter oxydans*, e.g. *Gluconobacter oxydans* DSM 4025, which had been deposited as DSM 4025 on Mar. 17, 1987 under the conditions of the Budapest Treaty at the Deutsche Sammlung von Mikroorganismen und Zellkulturen GmbH, Braunschweig, BRD, *Gluconobacter oxydans* subsp. *sphaericus, Gluconobacter roseus, Gluconobacter rubiginosus, Gluconobacter suboxydans*, mammalian cells and plant cells.

For expression, other regulatory elements, such as a Shine-Dalgarno (SD) sequence (for example, AGGAGG etc. including natural and synthetic sequences operable in the host cell) and a transcriptional terminator (inverted repeat structure including any natural and synthetic sequence operable in the host cell) which are operable in the host cell(into which the coding sequence will be introduced to provide a recombinant organism of this invention) can be used with the above described promoters.

For the expression of membrane-bound polypeptides, like the SLDH protein of the present invention, a signal peptide, which contains usually 15 to 50 amino acid residues and is totally hydrophobic, is preferably associated. A DNA encoding a signal peptide can be selected from any natural and synthetic sequence operable in the desired host cell.

A wide variety of host/cloning vector combinations may be employed in cloning the double stranded DNA. The cloning vector is generally a plasmid or phage which contains a replication origin, regulatory elements, a cloning site including a multi-cloning site and selection markers such as antibiotic resistance genes including resistance genes for ampicillin, tetracycline, kanamycin, streptomycin, gentamicin, spectinomycin etc.

Preferred vectors for the expression of the gene of the present invention in *E. coli* is selected from any vectors usually used in *E. coli*, such as pBR322 or its derivatives including pUC18 and pBluescript II (Stratagene Cloning Systems, Calif., USA), pACYC177 and pACYC184 (J. Bacteriol., 134:1141–1156, 1978) and their derivatives, and a vector derived from a broad host range plasmid such as RK2 (C. M. Thomas, Plasmid 5: 10, 1981) and RSF1010 (P. Guerry et al., J. Bacteriol. 117: 619–630, 1974). A preferred vector for the expression of the nucleotide sequence of the present invention in bacteria including Gluconobacter, Acetobacter and *P. putida* is selected from any vectors which can replicate in Gluconobacter, Acetobacter and/or *P. putida*, as well as in a preferred cloning organism such as *E. coli*. The preferred vector is a broad-host-range vector such as a cosmid vector like pVK100 (V. C. Knauf et al., Plasmid 8: 45–54, 1982) and its derivatives and RSF1010. Copy number and stability of the vector should be carefully considered for stable and efficient expression of the cloned gene and also for efficient cultivation of the host cell carrying the cloned gene (e.g.a recombinant organism os this invention). DNA molecules containing transposable elements such as Tn5 can be also used as a vector to introduce the desired gene into the preferred host, especially on a chromosome. DNA molecules containing any DNAs isolated from the preferred host together with the gene of the present invention is also useful to introduce this gene into the preferred host, especially on a chromosome. Such DNA molecules can be transferred to the preferred host by applying any of a conventional method, e.g. transformation, transduction, transconjugation or electroporation, which are well known to those skilled in the art, considering the nature of the host and the DNA molecule.

Useful hosts may include microorganisms, mammalian cells, and plant cells and the like. As a preferable microorganism, there may be mentioned bacteria such as *E. coli, P. putida, A. xylinum, A. pasteurianus, A. aceti, A. hansenii, Gluconobacter albidus, Gluconobacter capsulatus, Gluconobacter cerinus, Gluconobacter dioxyacetonicus, Gluconobacter gluconicus, Gluconobacter industrius, Gluconobacter melanogenus, Gluconobacter nonoxygluconicus, Gluconobacter oxydans, Gluconobacter oxydans* subsp. *sphaericus, Gluconobacter roseus, Gluconobacter rubiginosus, Gluconobacter suboxydans*, and any bacteria which are capable of expressing recombinant SLDH and/or ORF2 gene(s). Functional equivalents, subcultures, mutants and variants of said microorganism can be also used in the present invention. A preferred strain is *E. coli* K12 or its derivatives, *P. putida*, Gluconobacter or Acetobacter strains.

Figure 4:
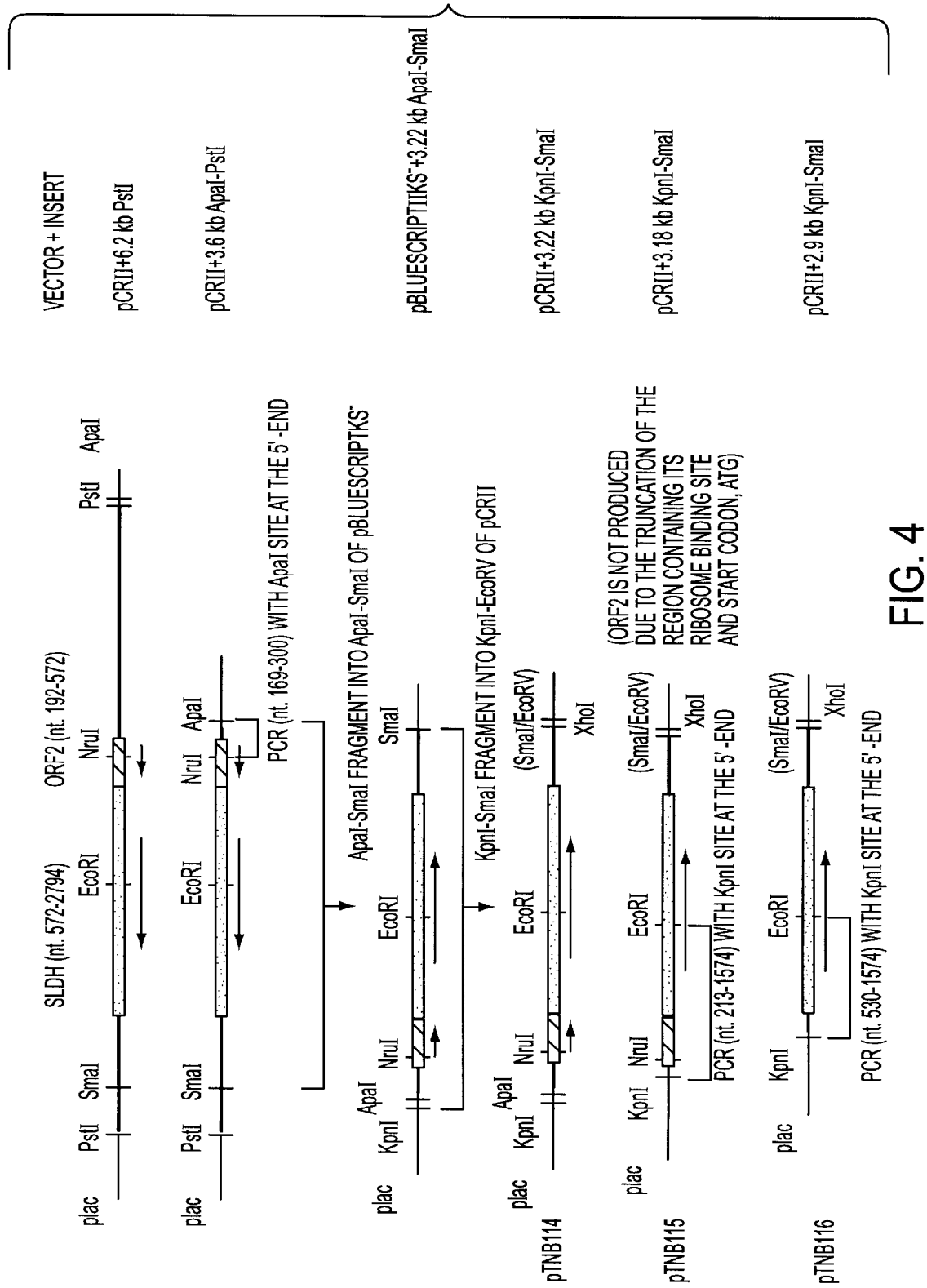
FIG. 4 illustrates the steps for constructing plasmids pTNB114, pTNB115, and pTNB116 for the expression of SLDH and/or ORF2 genes in *E. coli* under the control of lac promoter.
Figure 5:
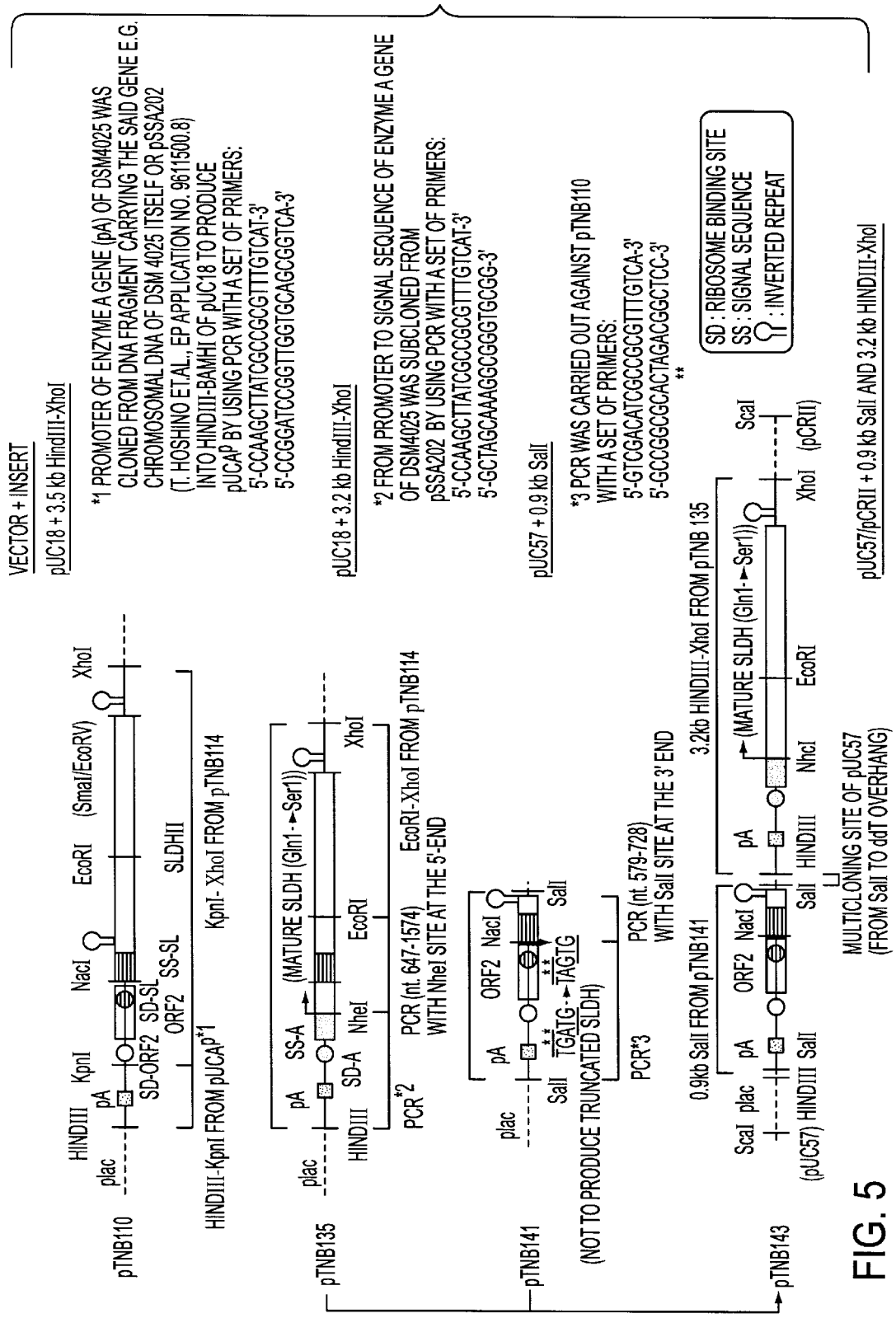
FIG. 5 illustrates the steps for constructing plasmids pTNB110 which carries ORF2 and SLDH genes under the control of common pA promoter (described below in Example 6) and pTNB143 which carries ORF2 gene under the control of pA located adjacent to the gene in the upstream and SLDH gene under the control of another pA promoter located adjacent to the SLDH gene in its upstream.

The SLDH and/or ORF2 gene(s)/nucleotide sequences provided in this invention are ligated into a suitable vector containing a regulatory region such as a promoter, a ribosomal binding site and a transcriptional terminator operable in the host cell described above with a well-known methods in the art to produce an expression vector. When the SLDH and ORF2 genes are cloned in combination, the two genes can be cloned either in tandem or separately on the same plasmid and also on the chromosomal DNA. FIGS. 4 and 5 exemplifies the form of the combined cloning of SLDH and ORF2 genes on the plasmid. One may clone also one gene on a plasmid and the other one on chromosomal DNA.

To construct a recombinant microorganism carrying a recombinant expression vector, various gene transfer methods including transformation, transduction, conjugal mating (Chapters 14 and 15, Methods for general and molecular bacteriology, Philipp Gerhardt et al. ed., American Society for Microbiology, 1994), and electroporation can be used. The method for constructing a recombinant organism may be selected from the methods well-known in the field of molecular biology. Usual transformation systems can be used for *E. coli*, Pseudomonas, Gluconobacter and Acetobacter. A transduction system can also be used for *E. coli*.

Conjugal mating system can be widely used in Gram-positive and Gram-negative bacteria including *E. coli, P. putida* and Gluconobacter. A preferred conjugal mating is disclosed in WO89/06688. The conjugation can occur in liquid medium or on a solid surface. The preferred recipient for SLDH and/or ORF2 production is selected from *E. coli, P. putida*, Gluconobacter and Acetobacter. To the recipient for conjugal mating, a selective marker is usually added; for example, resistance against nalidixic acid or rifampicin is usually selected. Natural resistance can be also used; e.g. resistance against polymyxin B is useful for many Gluconobacters.

The present invention provides recombinant SLDH. One can increase the production yield of the SLDH enzyme by introducing the gene of SLDH provided by the present invention into organisms including acetic acid bacteria including the genus Gluconobacter and the genus Acetobacter. One can also produce active SLDH in microorganisms beside Gluconobacter by using the SLDH gene of the present invention in combination with the ORF2 gene of the present invention. The recombinant SLDH can be immobilized on a solid carrier for solid phase enzyme reaction. The present invention also provides recombinant organisms. One can produce L-sorbose from D-sorbitol with the recombinant organisms. One can also produce L-sorbose from D-sorbitol even in a host organism beside acetic acid bacteria by introducing the SLDH gene in combination with the ORF2 gene of the present invention.

The Examples which follow are illustrative and are not intended to limit the invention in any way.

EXAMPLES

Example 1

Determination of amino acid sequences of SLDH (1) N-terminal amino acid sequence analyses of lysylendopeptidase-treated SLDH polypeptides Partial amino acid sequences of peptides No.1, 3 and 8 prepared from SLDH protein were determined (FIG. 1; SEQ ID NO:4 to 6). Purified SLDH of *G. suboxydans* IFO 3255 (T. Hoshino et al., EP 728840) was digested with lysylendopeptidase; the reaction mixture (25 ml) contained 1.2 mM of lysylendopeptidase and 3 nmol of the SLDH protein in 100 mM Tris-HCl buffer, pH9.0, and the reaction was carried out at 37° C. for 15 hours. The resulting peptide fragments were separated by HPLC (column : protein C-4, VYDAC, Calif., USA) with acetonitrile/isopropanol gradient in 0.1% TFA at a flow rate of 1.0 ml/min. Elution of the peptides was monitored by UV absorbance at 214 nm, and the peak fractions were collected manually and subjected to N-terminal amino acid sequence analysis with an amino acid sequencer (Applied Biosystems model 470A, The Perkin Elmer Corp., Conn., USA).

Example 2

Cloning of partial SLDH gene by PCR

PCR was conducted with chromosomal DNA of *G. suboxydans* IFO 3255 and degenerate oligonucleotide DNA primers, s7 and s6R whose sequences are shown in FIG. 1. The PCR amplification was carried out with thermostable polymerase Amplitaq (Perkin-Elmer, Roche Molecular Systems Inc., N.J., USA), using a thermal cycler (ZYMOREACTOR II AB-1820, ATTO, Tokyo, Japan). The following reaction mixture (50 $\mu$l) was used for PCR: 200 $\mu$M of dNTPs, 10~20 pmol of each primer (54~288 degeneracy), 6 ng of chromosomal DNA of *G. suboxydans* IFO 3255 and 0.5 unit of the DNA polymerase in the buffer provided from the supplier. The reaction consisted of 30 cycles of 1) denaturation step at 94° C. for 1 min; 2) annealing step at 48° C. for 1 min; 3) synthesis step at 72° C. for 2 min. Consequently, 1.6 kb DNA was amplified and cloned in E. coli vector, pUC57/T (MBI Fermentas, Vilnius, Lithuania), which has 3'-ddT-tailed ends for direct ligation of an amplified DNA fragment to obtain a recombinant plasmid pMT20. The cloned DNA was subjected to nucleotide sequencing by the method of dideoxy-chain termination (F. Sanger et al, Proc. Natl. Acad. Sci. USA, 74:5463–5467, 1977); the 1.6 kb fragment encoded the peptides No. 3 and No. 8.

Example 3
Complete cloning of the SLDH gene (1) Construction of gene library of G. suboxydans IFO 3255

The chromosomal DNA of G. suboxydans IFO 3255 was prepared from the cells grown on MB agar plate for 2 days. The chromosomal DNA (160 µg) was partially digested with 20 units of Eco RI in 500 µl of reaction mixture. Portions of the sample were withdrawn at 5, 10, 15, 30, and 60 minutes and the degree of the digestion was detected by agarose gel electrophoresis. Former four portions which contained partially-digested DNA fragments were combined and subjected to preparative gel electrophoresis (agarose: 0.6%). Fragments of 15–35 kb were cut out and electroeluted from the gel. The eluate was filtered and precipitated with sodium acetate and ethanol at −80° C. The DNA fragments were collected by centrifugation and suspended in 200 µl of 10 mM Tris-HCl, pH8.0, buffer containing 1 mM EDTA.

In parallel, 1.8 µg of a cosmid vector pVK100 was completely digested with Eco RI and treated with calf intestine alkaline phosphatase. The linearized and dephosphorylated pVK100 was ligated with 15–35 kb Eco RI fragments of the chromosomal DNA of G. suboxydans IFO 3255 (5 µg) with the ligation kit (Takara Shuzo, Kyoto, Japan) in 20 separate tubes under the condition recommended by the supplier to obtain highly polymerized DNA. The ligated DNA was then used for in vitro packaging according to the method described by the supplier (Amersham Japan). The resulting phage particles were used to infect E. coli ED8767, a host for the genomic library. Consequently, 4,271 colonies were obtained and all of the colonies tested (20 colonies) possessed the insert DNAs with the average size of about 25 kb.

(2) Colony hybridization to obtain complete SLDH gene

The cosmid library described above was screened to isolate the clone carrying complete SLDH gene by colony hybridization method with $^{32}$P-labeled 1.6 kb DNA of pMT20. One clone was isolated and designated pSLII, which carry about 25 kb insert in pVK100 vector. From the pSLII, 6.2 kb Pst I fragment was isolated and cloned into pUC18 to obtain plasmid pUSLIIP. The 6.2 kb Pst I fragment containing ORF2 and SLDH genes was isolated from pUSLIIP and subcloned into pCRII vector (Invitrogen Corporation, Calif., USA) to produce pCRSLIIP. From the resulting plasmid, the DNA fragment containing the 6.2 kb Pst I fragment was isolated as Hind III-Xho I fragment and cloned between Hind III and Xho I sites of pVK100 to obtain pVKSLIIP.

(3) Expression of SLDH gene in E. coli

To confirm whether 6.2 kb Pst I-fragment encodes the target SLDH, cells of E. coli JM109 carrying pUSLIIP was subjected to Western-blot analysis with anti-SLDH antibody as described above. Immuno-positive proteins with a molecular weight of about 80 kDa were observed in the transformant, indicating that the Pst I-fragment encodes the polypeptides with the molecular weight of the intact SLDH (79 kDa +/−0.5 kDa).

(4) Construction of SLDH-deficient Gluconobacter, strain 26A11, as the test strain for SLDH-activity complementation Transposon Tn5 mutagenesis was performed with G. melanogenus IFO 3293 as the parent. Tn5, a transposable element coding for Kmr, causes null mutations at random on DNA of its host organism and widely used as a mutagen in Gram-negative bacteria. The IFO 3293 was selected as the parent in the following reasons: (i) it produced L-sorbose from D-sorbitol, (ii) it showed immuno-positive polypeptide of about 80 kDa in Western-blot analysis with the antibody prepared against SLDH purified from G. suboxydans IFO 3255 and (iii) its frequency for generating Tn5 mutants was much higher than that of G. suboxydans IFO 3255.

G. melanogenus IFO 3293 was cultivated in a test tube containing 5 ml of the MB medium containing 25 g/l of mannitol, 5 g/l of yeast extract (Difco Laboratories, ), 3 g/l of Bactopepton (Difco) at 30° C. overnight. E. coli HB101 (pRK2013) [D. H. Figurski, Proc, Natl. Acad. Sci. USA 76: 1648–1652, 1979] and E. coli HB101 (pSUP2021) [R. Simon, et al., BIO/TECHNOL. 1:784–791, 1983] were cultivated in test tubes containing 5 ml of LB medium with 50 µg/ml of kanamycin at 37° C. overnight. The cells was separately collected by centrifugation and suspended in the half volume of MB medium. The each cell suspension was mixed in the ratio of 1:1:1 and the mixture was placed on the nitrocellulose filter on the surface of MB agar plate. The plate was incubated at 27° C. overnight and the resulting cells on the filter was scraped, suspended in the appropriate volume of MB medium and spread on the selection plate (MPK plate), MB containing 10 µg/ml of polymyxin B and 50 µg/ml of kanamycin. The MPK plate was incubated at 27° C. for 3 to 4 days.

The resulting 3,436 Tn5 mutants were subjected to the immuno-dot blot screening with the anti-SLDH antibody. The cells of each strain were independently suspended in 50 µl Laemmli buffer consisting of 62.5 mM Tris-HCl (pH6.5), 10% glycerol, 2% SDS and 5% β-mercaptoethanol in 96-well microtiter plate and incubated at 60° C. for 2 hours. The Cell Free Extracts (CFEs) were stamped on the nitrocellulose filter and the immuno-positive samples in the CFEs were screened with AP conjugate substrate kit (Bio-RAD Laboratories, Richmond, Calif., USA). As a result, only one strain 26A11 without positive signal in the immuno-dot blot screening was obtained.

SLDH-deficiency of the strain 26A11 was confirmed by Western-blot analysis; it expressed at most 1/500 amount of SLDH compared with its parent strain. 26A11 was not a complete SLDH-deficient strain but the strain with SLDH gene repressed by Tn5 insertion; the insertion site was found to be close to the C-terminus by determining the nucleotide sequence around Tn5-insertion point. Next, a resting cell reaction was conducted to examine the whole SLDH activity in 26A11 and the wild Gluconobacter strains. In the potassium phosphate buffer 100 mM (pH7.0) containing 2% D-sorbitol, 26A11 slightly converted D-sorbitol to L-sorbose, whereas the wild strains IFO 3293 and IFO 3255 completely did it in 39.5 hr at 30° C.

(5) Expression of SLDH gene in 26A11

To confirm the SLDH activity of the SLDH clones obtained, complementation test was conducted. Plasmids pSLII and pVKSLIIP were introduced into 26A11 by a conjugal mating. The transconjugant carrying pSLII or pVKSLIIP restored the activity of SLDH in a mini-resting cell reaction and showed immuno-reactive polypeptide of about 80 kDa in Western-blot analysis.

(6) Nucleotide sequencing of the SLDH gene

Plasmid pUSLIIP was used for nucleotide sequencing of SLDH and ORF2 genes. Determined nucleotide sequence (SEQ ID NO: 1; 3,481 bp) revealed that ORF of SLDH gene (2,223 bp, nucleotide No. 572 to 2794 in SEQ ID NO: 1) encoded the polypeptide of 740 amino acid residues (SEQ ID NO: 2), in which there were three amino acid sequences (Peptides No. 1, 3, and 8 shown in SEQ ID NO: 4 to 6) determined from the purified SLDH polypeptide. In addition to the SLDH ORF, one more ORF, ORF2, was found just upstream of SLDH ORF as illustrated in FIGS. 2 and 3. The ORF of ORF2 (381 bp, nucleotide No. 192 to 572 in SEQ ID NO: 1) encoded the polypeptide of 126 amino acid residues (SEQ ID NO. 3).

The 4$^{th}$ amino acid sequence of Peptide No.1 was determined as Glu by the amino acid sequencer, but it was Ala according to the DNA sequence. The 11$^{th}$ amino acid sequence of Peptide No.3 was determined as Gln by the amino acid sequencer, but it was Pro according to the DNA sequence. A signal peptide-like region (SEQ ID NO: 8) is possibly included in the deduced amino acid sequence: it contains (i) many hydrophobic residues, (ii) a positively-charged residues near N-terminus, and (iii) Ala-Xaa-Ala site as a cleaved signal. The actual signal sequence was determined as described in Example 3 (7). The putative ribosome-binding site (Shine-Dalgarno, SD, sequence) for SLDH gene was located at 8 bp upstream of the initiation codon (AGAGGAG at nucleotide No. 558–564 of Seq ID NO: 1). The putative SD sequence for ORF2 gene was located at 10 bp upstream of the initiation codon (GGGAGG at nucleotide No. 177 to 182 of Seq ID NO: 1). There were some inverted repeat sequences immediately downstream the SLDH structure gene (nucleotide sequences of No. 2803–2833 and of No. 2838–2892) as illustrated in FIG. 3; they may function as transcription termination loops for SLDH gene. For ORF2 gene, the inverted repeat sequence was found at No. 684–704.

Homology search for SLDH and ORF2 was performed with the programs of mpBlast (NCBI, Bethesda, Md. USA) and Motifs in GCG (Genetics Computer Group, University Research Park, Wis., USA). SLDH polypeptide had the sequence commonly conserved in quinoprotein at the region near C-terminus (within amino acid residue No. 632 to 692 of SEQ ID No. 2) and the other sequence identified as a quinoprotein motifs (Prosite No. PS00363: [DN]W.{3}G [RK].{6}[FY]S.{4}[LIVM]N.{2}NV.{2}L[RK]; amino acid residue No. 79 to 107 of SEQ ID No. 2).

ORF2 showed homology with the N-terminal region of the membrane-bound PQQ-dependent D-glucose dehydrogenase (GDH) of *G. oxydans, E. coli, Acinetobacter calcoaceticus*, which is known as a membrane-spanning region to bind the GDH to the membrane. Identities of ORF2 to the N-terminal region of the GDHs of *G. oxydans, E. coli, A. calcoaceticus* were 30%, 32%, and 37%, respectively. The ORF2 protein may function as an anchoring protein to make the SLDH membrane-bound type.

Example 4

Determination of N-terminal and C-terminal sequences of mature SLDH polypeptide

Direct sequencing of the N-terminus gave no results, indicating that the N-terminus is blocked. Then, SLDH polypeptide was treated with the endoproteinase Lys-C (Wako, Osaka Japan ) in 0.1 M Tris-HCl at 37° C. for 20 hours with a substrate-to-enzyme ratio of 20:1 (w/w). Total digest was analyzed by reversed phase HPLC (RP300, 1 mm×25 cm, Applied Biosystems, Foster City, Calif.) and each peak was subjected to mass spectrometry (TSQ700 triple quadrupole instrument, Finnigan-MAT, San Jose, Calif.) for determining molecular weight. One of the digest described as SEQ ID No. 7 was assigned as the N-terminal sequence by the mass spectrometric analysis and amino acid composition analysis together with the amino acid composition predicted from determined nucleotide sequence shown as SEQ ID NO: 1. Further analysis with collisional induced dissociation (CID) was carried out to confirm the identity of the peptide with N-terminal sequence. The N-terminus was determined to be pyroglutamyl residue.

Since the N-terminus of SLDH was determined to be Gln-Phe-Ala-Pro-Ala-Gly-Ala-Gly-Gly-Glu-Pro-Ser-Ser-Ser-Val-Pro-Gly-Pro-Gly-Asn-Ala-Ser-Glu-Pro-Thr-Glu-Asn-Ser-Pro-Lys as shown in SEQ ID NO. 7, the signal sequence was confirmed to be 24 amino acid residue long with the sequence of Met-Arg-Arg-Pro-Tyr-Leu-Leu-Ala-Thr-Ala-Ala-Gly-Leu-Ala-Leu-Ala-Cys-Ser-Pro-Leu-Ile-Ala-His-Ala as listed as SEQ ID NO: 8. The C-terminal sequence was also determined by using the peptide recovered from V8 protease digest to be Pro-Asp-Ala-Ile-Lys-Gln (SEQ ID NO: 9).

Example 5

Expression of the SLDH and/or ORF2 gene(s) in *E. coli*

From the pCRSLIIP described in Example 3 (2), plasmids carrying SLDH gene with or without ORF2 gene under the lac promoter control were constructed as illustrated in FIG. 4. The resulting three plasmids are pTNB114 carrying SLDH and ORF2 genes, pTNB115 carrying SLDH gene and ORF2 gene truncated at its N-terminus containing ribosome binding site and start codon (ATG) and pTNB116 carrying mostly-truncated ORF2 gene and intact SLDH gene. These three plasmids were introduced into *E. coli* by conventional transformation. The production of the SLDH polypeptide was detected by Western-blot analysis with cell free extracts of the resulting transformants and the SLDH activity was assayed with resting cells. The resting cell reaction was carried out in the reaction mixture consisting of 0.3% NaCl, 1% $CaCO_3$, 4% D-sorbitol, and 1 mM PMS with or without 1 μg/ml of PQQ at room temperature for 17 hours. The SLDH activity to produce L-sorbose was analyzed by TLC assay with Silica gel 60 $F_{254}$, 0.25 mm, Merck with the developing solvent consisting of n-propanol-$H_2O$-1% $H_3PO_4$-HCOOH (400:100:10:1) and spray reagent of naphthoresorcinol. Consequently, SLDH polypeptide was detected in all transformants, even without ORF2 gene expression, in Western-blot analysis, but SLDH activity to produce L-sorbose was detected only in transformant carrying pTNB114 containing intact ORF2 gene under the resting cell reaction condition in the presence of PQQ.

Example 6

Expression of the SLDH and/or ORF2 gene(s) in *E. coli*

FIG. 5 illustrates construction steps of pTNB110 and pTNB143. Plasmid pTNB110 carrying ORF2 and SLDH genes under control of the promoter of Enzyme A gene (pA) of DSM4025 (T. Hoshino et al., European Patent Application No. 9611500.8) was constructed by inserting Hind III-Kpn I fragment containing pA, Kpn I-Xho I fragment from pTNB114 between Hind III-Xho I of pUC18. Plasmid pTNB143 carrying ORF2 and SLDH genes as independent expression units, ORF2 gene with pA and SLDH gene with pA, was constructed by inserting 0.9 kb Sal I fragment from pTNB141 and 3.2 kb Hind III-Xho I fragment from pTNB135 into pUC57/pCRII hybrid vector (Sca I-Hind III fragment with plac from pUC57 and Xho I to Sca I fragment without plac from pCRII) as shown in FIG. 5. The plasmids, pTNB110 and pTNB143, were introduced into *E. coli* by conventional transformation. The resulting transformants were subjected to Western-blot analysis and resting cell reaction as described in Example 5. Consequently, both of the transformants carrying pTNB110 and pTNB143 produced SLDH protein and showed SLDH activity to produce L-sorbose from D-sorbitol in the presence of PQQ.

Example 7
Expression of the SLDH gene in *G. oxydans* DSM 4025

The plasmid pTNB136 for the expression of SLDH gene in *G. oxydans* DSM 4025 having strong L-sorbose and L-sorbosone dehydrogenase activities together with weak D-sorbitol dehydrogenase activity to produce L-sorbose, was constructed by inserting Hind III-Xho I fragment from pTNB135 (FIG. 5) between Hind III and Xho I sites of pVK100. The plasmid pTNB136 and its vector pVK100 were introduced by conjugal mating into strain GOBΔK, which is a mutant of *G. oxydans* DSM 4025 whose gene of Enzyme B (EP 832 974) having D-sorbitol dehydrogenase to produce L-sorbose is deleted by replacing two Eco RI fragments containing Enzyme B gene with kanamycin resistant gene cassette (1.28 kb Eco RI fragment of pUC4K; Pharmacia Uppsala, Sweden). The gene disruption was conducted by the recombinant DNA techniques well-known in the art. The resulting transconjugant, GOBΔK carrying pTNB136 or pVK100, produced 5 g/L or below 2 g/l of 2KGA in 10% D-sorbitol, respectively, by flask fermentation conducted at 30° C. for 4 days (medium: 10% D-sorbitol, 1.6% urea, 0.05% glycerol, 0.25% $MgSO_4.7H_2O$, 3% corn steep liquor, 6.25% baker's yeast wet cells and 1.5% $CaCO_3$). Western-blot analysis with anti-SLDH antibody revealed that the transconjugants carrying pTNB136 expressed the immuno-reactive SLDH polypeptides.

What is claimed is:

1. An isolated polynucleotide fragment encoding a D-sorbitol dehydrogenase obtained from *Gluconobacter suboxydans*.

2. An isolated polynucleotide fragment comprising the nucleotide sequence of SEQ ID NO:1 or a fragment of SEQ ID NO:1 encoding D-sorbitol dehydrogenase activity.

3. An isolated polynucleotide fragment according to claim 2 wherein the polynucleotide consists of SEQ ID NO:1.

4. An isolated polynucleotide fragment selected from the group consisting of (a) nucleotides 192 to 569 of SEQ ID NO:1, (b) nucleotides 644 to 2791 of SEQ ID NO:1, (c) nucleotides 572 to 2791 of SEQ ID NO:1, and combinations of (a) and (b) and (a) and (c).

5. An isolated polynucleotide fragment according to claim 4 consisting of nucleotides 192 to 569 of SEQ ID NO:1.

6. An isolated polynucleotide fragment according to claim 4 consisting of nucleotides 644 to 2791 of SEQ ID NO:1.

7. An isolated polynucleotide fragment according to claim 4 consisting of nucleotides 572 to 2791 of SEQ ID NO:1.

8. An isolated polynucleotide fragment according to claim 4 comprising nucleotides 192 to 569 and 644 to 2791 of SEQ ID NO:1.

9. An isolated polynucleotide fragment according to claim 4 comprising nucleotides 192 to 569 and 572 to 2791 of SEQ ID NO:1.

10. An isolated polynucleotide fragment comprising a polynucleotide selected from the group consisting of 572 to 2791 of SEQ ID NO:1 and a polynucleotide encoding the polypeptide of SEQ ID NO:3.

11. An isolated polynucleotide fragment comprising a polynucleotide selected from the group consisting of 644 to 2791 of SEQ ID NO:1 and a polynucleotide encoding the polypeptide of SEQ ID NO:3.

12. An isolated polynucleotide fragment comprising a polynucleotide selected from the group consisting of a polynucleotide fragment encoding amino acid positions 1 to 716 of SEQ ID NO:2 and a polynucleotide consisting of nucleotides 192–569 of SEQ ID NO:1.

13. An isolated polynucleotide fragment selected from the group consisting of a polynucleotide encoding a polypeptide consisting of amino acids 1–716 of SEQ ID NO:2 and a polynucleotide encoding the polypeptide of SEQ ID NO:3.

14. An isolated polynucleotide fragment encoding a polypeptide consisting of the amino acid sequence of SEQ ID NO:2.

15. An isolated polynucleotide fragment according to claim 14 which encodes a polypeptide consisting of amino acid positions 1 to 716 of SEQ ID NO:2.

16. An isolated polynucleotide fragment encoding a polypeptide consisting of the amino acid sequence of SEQ ID NO:3.

17. A microorganism containing a recombinant polynucleotide fragment encoding a D-sorbitol dehydrogenase obtained from *Gluconobacter suboxydans*.

18. A microorganism containing a recombinant polynucleotide fragment comprising SEQ ID NO:1 or a fragment of SEQ ID NO:1 encoding D-sorbitol dehydrogenase activity.

19. A microorganism containing a recombinant polynucleotide fragment selected from the group consisting of (a) nucleotides 192 to 569 of SEQ ID NO:1, (b) nucleotides 644 to 2791 of SEQ ID NO:1, (c) nucleotides 572 to 2791 of SEQ ID NO:1, and combinations of (a) and (b) and (a) and (c).

20. A microorganism according to claim 19 wherein the polynucleotide recombinant fragment comprises nucleotide residues 192 to 569 and 644 to 2791 of SEQ ID NO:1.

21. A microorganism according to claim 19 wherein the polynucleotide recombinant fragment comprises nucleotide residues 192 to 569 and 572 to 2791 of SEQ ID NO:1.

22. A microorganism according to claim 19 which is a member of a genus selected from the group consisting of Gluconobacter, Acetobacter, and *E. coli*.

23. A microorganism according to claim 19 wherein the recombinant polynucleotide fragment is integrated into the microorganism's chromosomal DNA.

24. A microorganism comprising a recombinant polynucleotide fragment selected from the group consisting of a polynucleotide encoding a polypeptide consisting of amino acids 1–716 of SEQ ID NO:2 and a polynucleotide encoding the polypeptide of SEQ ID NO:3.

25. An expression vector comprising a polynucleotide fragment encoding a D-sorbitol dehydrogenase obtained from *Gluconobacter suboxydans*.

26. An expression vector containing a polynucleotide fragment comprising SEQ ID NO:1 or a fragment of SEQ ID NO:1 encoding D-sorbitol dehydrogenase activity.

27. An expression vector containing a polynucleotide fragment selected from the group consisting of (a) nucleotides 192 to 569 of SEQ ID NO:1, (b) nucleotides 644 to 2791 of SEQ ID NO:1, (c) nucleotides 572 to 2791 of SEQ ID NO:1, and combinations of (a) and (b) and (a) and (c).

28. An expression vector according to claim 27 wherein the polynucleotide fragment is selected from the group consisting of nucleotides 192 to 569 and 644 to 2791 of SEQ ID NO:1.

29. An expression vector according to claim 27 wherein the polynucleotide fragment is selected from the group consisting of nucleotides 192 to 569 and 572 to 2791 of SEQ ID NO:1.

30. An expression vector comprising a polynucleotide fragment selected from the group consisting of a polynucleotide encoding a polypeptide consisting of amino acids 1–716 of SEQ ID NO:2 and a polynucleotide encoding the polypeptide of SEQ ID NO:3.

31. A process for producing recombinant D-sorbitol dehydrogenase comprising cultivating a microorganism containing a polynucleotide fragment encoding a D-sorbitol dehydrogenase obtained from *Gluconobacter suboxydans* in a culture medium under conditions permitting expression of D-sorbitol dehydrogenase.

32. A process for producing recombinant D-sorbitol dehydrogenase comprising cultivating a microorganism containing a polynucleotide fragment comprising SEQ ID NO:1 or a fragment of SEQ ID NO:1 encoding D-sorbitol dehydrogenase activity in a culture medium under conditions permitting expression of D-sorbitol dehydrogenase.

33. A process for producing recombinant D-sorbitol dehydrogenase comprising cultivating a microorganism containing a polynucleotide selected from the group consisting of (a) nucleotides 192 to 569 of SEQ ID NO: 1, (b) nucleotides 644 to 2791 of SEQ ID NO: 1, (c) nucleotides 572 to 2791 of SEQ ID NO: 1, and combinations of (a) and (b) and (a) and (c).

34. A process for producing recombinant D-sorbitol dehydrogenase according to claim 33 wherein the polynucleotide fragment is selected from the group consisting of nucleotides 192 to 569 and 644 to 2791 of SEQ ID NO:1.

35. A process for producing recombinant D-sorbitol dehydrogenase according to claim 33 wherein the polynucleotide fragment is selected from the group consisting of nucleotides 192 to 569 and 572 to 2791 of SEQ ID NO:1.

36. A process for producing recombinant D-sorbitol dehydrogenase according to claim 33 wherein the polynucleotide fragment is selected from the group consisting of a polynucleotide that encodes a polypeptide consisting of amino acids 1–716 of SEQ ID NO:2 and a polynucleotide encoding the polypeptide of SEQ ID NO:3.

37. A process for producing recombinant D-sorbitol dehydrogenase comprising cultivating a microorganism comprising the expression vector of claim 26.

* * * * *

UNITED STATES PATENT AND TRADEMARK OFFICE
CERTIFICATE OF CORRECTION

PATENT NO      :   6,127,156

DATED          :   October 3, 2000

INVENTOR(S)    :   Tatsuo HOSHINO, et al.

It is certified that error appears in the above-identified patent and that said Letters Patent are hereby corrected as shown below:

On the title page, under "[75] Inventors," please change both instances of "Kamakura" to --Kamakura-shi--, and both instances of "Fujisawa" to --Fujisawa-shi--.

Signed and Sealed this

Twenty-second Day of May, 2001

*Attest:*

NICHOLAS P. GODICI

*Attesting Officer*      *Acting Director of the United States Patent and Trademark Office*

UNITED STATES PATENT AND TRADEMARK OFFICE
CERTIFICATE OF CORRECTION

PATENT NO.    : 6,127,156
DATED         : October 3, 2000
INVENTOR(S)   : Tatsuo Hoshino et al.

It is certified that error appears in the above-identified patent and that said Letters Patent is hereby corrected as shown below:

Column 27,
Line 58, please delete "amino acid positions 1 to 716 of";
Line 63, please delete "amino acids 1-716 of";

Column 28,
Lines 24-26, please cancel Claim 15.
Line 58, please delete "amino acids 1-716 of";

Column 29,
Line 14, please delete "amino acids 1-716 of";

Column 30,
Line 20, please delete "amino acids 1-716 of";

Signed and Sealed this

Twenty-fourth Day of September, 2002

Attest:

Attesting Officer

JAMES E. ROGAN
Director of the United States Patent and Trademark Office

SEQUENCE LISTING

<160> NUMBER OF SEQ ID NOS: 9

<210> SEQ ID NO 1
<211> LENGTH: 3481
<212> TYPE: DNA
<213> ORGANISM: Gluconobacter suboxydans

<400> SEQUENCE: 1

```
acaaatcata ctggcggcgc tgtagtgaca attccggcgg gttaaagaga atattttttt      60
ggtgacaggc cacaacaaat ttttgttacc tcaaacacag ttttgttaga gcatttgaaa     120
acgaagtccg atggacctga actgaatatg gatttaccgt ccggaggatt cagtttggga     180
ggcattcggt tatgccaaat cttcaaggta ataggactct gacggagtgg ctgacgctgc     240 ttctcgggggt catcgtcctt cttgtgggcc tgttcttcgt cattgggggt gctgacctcg     300
cgatgctggg cggctctacc tactatgttc tctgtggcat cctcctggtt gctagcggcg     360
tattcatgct catgggccgc acgcttggtg ccttcctgta tctgggtgcc ctggcctaca     420
cgtgggtctg gtccttctgg gaagtcggtt tcagcccccat cgatcttctg ccccgcgctt     480
tcggcccgac catccttggc attctcgttg ccctgaccat tccggtcctg cgccgcatgg     540
aaagccgtcg tactctcaga ggagccgtct gatgcgccgg ccttaccttc tagcaacagc     600
cgcaggactc gcccttgcct gttcgccgct catcgctcat gcacagtttg ctcccgcagg     660
ggctggcggc gaaccttcct cgtcagttcc tgggccagga aatgcgagcg agcccaccga     720
aaactctccg aaaagtcaga gctacttcgc aggaccgtcg ccctatgccc cgcaggctcc     780
tggcgtaaac gcagccaacc tgccggacat tgagtcaatc gatccctcgc aggtcccggc     840
catggctccg cagcagagtg ccaatccggc acgtggagac tgggttgctt acggacgtga     900
cgatcatcag acgcgatact ctccgctttc ggaaatcacg cctgagaacg caagcaagct     960
caaggtcgct ttcgtctacc acacgggggag ttatccgcgt ccgggacagg tgaacaaatg    1020
ggccgccgaa accacgccga tcaaggttgg tgacggtctc tacacatgtt ccgccatgaa    1080
cgacatcatc aagctggatc cggctacggg taagcagatc tggcgtcgga acgtggatgt    1140
caaataccac tccattccct ataccgctgc ctgtaagggt gtgacgtatt tcacgtcctc    1200
cgtggtgccg gaaggccagc cctgccacaa tcgccttatc gaaggcacgc tggatatgcg    1260
tctgattgcg gttgacgcgg agacagggga tttctgccct aatttcggtc atggtggtca    1320
ggtcaacctg atgcagggtc tgggtgagtc tgttccgggc ttcgtctcca tgacggcacc    1380
```

```
tccaccggtc atcaacggcg tcgtggttgt aaaccacgaa gtgctcgacg gtcagcgccg    1440
ctgggctccg tccggtgtga tccgtggtta cgatgctgaa agtggcaaat tcgtatgggc    1500
ctgggacgtc aacaattccg gacgatcaca gccagcctac cggtaaccg tcattacagc    1560 cgtggaacgc cgaattcctg gctacctga caggcgacaa cgaggaggt ctcgtttacg    1620 tcccgacagg aactctgctg ctgactatta cagcgccctg cgtagtgatg ctgaaaacaa    1680
ggtgtcctcc gctgttgtcg ccattgacgt caagacgggt tctccgcgct gggtcttcca    1740
gacggctcat aaggacgtct gggattatga catcggttca caggcgaccc tgatggatat    1800
gcctggcccg gatggccaga cggttcctgc tctcatcatg ccgaccaagc gtggccagac    1860
gttcgtgctt gaccgtcgta ccggcaagcc aattctgccg gttgaagaac gcccagctcc    1920
gtcccctggt gttattccgg gtgacccgcg ttctccgacg cagccatggt ccgtcgggat    1980 gccggcccctt cgcgtgccgg atctgaaaga gacagacatg tggggtatgt cccccatcga    2040
tcagctcttc tgccgtatca agttccgccg tgcgaactat gtgggtgagt tcacaccacc    2100
gagcgttgac aagccgtgga ttgaatatcc gggctataac ggtggcagtg actgggctc    2160 catgtcctat gatccgcagt ccggcatcct gattgcgaac tggaacatca caccgatgta    2220
cgaccagctc gtaacccgca agaaggcaga ctccctcggc ctgatgccga tcgatgaccc    2280
caacttcaag ccaggtggcg gtggtgccga aggtaacggc gccatggacg gaacgcctta    2340
cggtatcgtc gtgacaccgt tctgggatca gtacacgggc atgatgtgca accgtccgcc    2400
ctacggtatg atcacagcca tcgacatgaa gcacggccag aaggttctgt ggcagcatcc    2460
gctcggaacg gctcgcgcca acgtccatg gggtctgcca acaggtctgc catgggaaat    2520
cggcactccg aacaatggtg gttcggttgt gaccggtggc ggtctgatct tcatcggtgc    2580
ggcaacggat aaccagatcc gcgcgattga tgaacacact ggcaaggttg tctggagcgc    2640
agtcctcccc ggcggcggtc aggccaatcc gatgacgtat gaagccaatg gtcaccagta    2700
cgttgccatc atggctggcg gtcatcactt catgatgacg ccagtgtctg accagcttgt    2760
ggtttacgca ctgccggatg ccatcaagca gtaattaagt cctgtggcgg atgtgtcatg    2820
catatccgcc acactccatc gtcagaagga gactttcgtg ctagccatgc agggaagtct    2880
ccttttgacg ttttttggctc tttccagcga gcgggcagtc tgaaacgggg cttcgtctgg    2940
ctcgtacttt cagaatggct cgtcgcaccc tcatgactgc ccactccccc gttatcttgc    3000
aggttctgcc agccctcagc acgggcggcc tggagcgggg agctattgaa attgcggctg    3060
ccatcacaca ggctggtggc aaggccattg tcgcttcgaa gacgggtcct cttcttgtgc    3120
aactccgcca cgtcggagca gtgcatgtgc cgctggatct caaatcgaaa tcgccgtttt    3180
ctgttcggcg ccgtgcccgt gaactccaga aactgatccg ggagcagcag gttgatctgg    3240
ttcacgcccg gtcccgtatt ccggcatggg ccgcctggct cgcctgccgc cgcgagaaca    3300
ttcctttcgt gacaacgtgg catggcgtcc acgaggctgg ctggtggggc aagaaattct    3360
acaattcggt gctggcccgg ggtgcaaggg tcatcgcaat ttcgcactac atttccgggc    3420
gtctttcagg gcagtacggc gttcaggcag atcgtcttcg aaccattccg cgtggtgccg    3480
a                                                                    3481
```

<210> SEQ ID NO 2  
<211> LENGTH: 739  
<212> TYPE: PRT  
<213> ORGANISM: Gluconobacter suboxydans  
<220> FEATURE:

```
<221> NAME/KEY: SIGNAL
<222> LOCATION: (1)..(24)

<400> SEQUENCE: 2
```

Met Arg Arg Pro Tyr Leu Leu Ala Thr Ala Gly Leu Ala Leu Ala
1               5                   10                  15

Cys Ser Pro Leu Ile Ala His Ala Gln Phe Ala Pro Gly Ala Gly
            20                  25                  30

Gly Glu Pro Ser Ser Ser Val Pro Gly Pro Gly Asn Ala Ser Glu Pro
        35                  40                  45

Thr Glu Asn Ser Pro Lys Ser Gln Ser Tyr Phe Ala Gly Pro Ser Pro
    50                  55                  60

Tyr Ala Pro Gln Ala Pro Gly Val Asn Ala Ala Asn Leu Pro Asp Ile
65                  70                  75                  80

Glu Ser Ile Asp Pro Ser Gln Val Pro Ala Met Ala Pro Gln Gln Ser
                85                  90                  95

Ala Asn Pro Ala Arg Gly Asp Trp Val Ala Tyr Gly Arg Asp Asp His
            100                 105                 110

Gln Thr Arg Tyr Ser Pro Leu Ser Glu Ile Thr Pro Glu Asn Ala Ser
        115                 120                 125

Lys Leu Lys Val Ala Phe Val Tyr His Thr Gly Ser Tyr Pro Arg Pro
130                 135                 140

Gly Gln Val Asn Lys Trp Ala Glu Thr Thr Pro Ile Lys Val Gly
145                 150                 155                 160

Asp Gly Leu Tyr Thr Cys Ser Ala Met Asn Asp Ile Ile Lys Leu Asp
                165                 170                 175

Pro Ala Thr Gly Lys Gln Ile Trp Arg Arg Asn Val Asp Val Lys Tyr
            180                 185                 190

His Ser Ile Pro Tyr Thr Ala Ala Cys Lys Gly Val Thr Tyr Phe Thr
        195                 200                 205

Ser Ser Val Val Pro Glu Gly Gln Pro Cys His Asn Arg Leu Ile Glu
    210                 215                 220

Gly Thr Leu Asp Met Arg Leu Ile Ala Val Asp Ala Glu Thr Gly Asp
225                 230                 235                 240

Phe Cys Pro Asn Phe Gly His Gly Gly Gln Val Asn Leu Met Gln Gly
                245                 250                 255

Leu Gly Glu Ser Val Pro Gly Phe Val Ser Met Thr Ala Pro Pro
            260                 265                 270

Val Ile Asn Gly Val Val Val Asn His Glu Val Leu Asp Gly Gln
            275                 280                 285

Arg Arg Trp Ala Pro Ser Gly Val Ile Arg Gly Tyr Asp Ala Glu Ser
        290                 295                 300

Gly Lys Phe Val Trp Ala Trp Asp Val Asn Asn Ser Gly Arg Ser Gln
305                 310                 315                 320

Pro Ala Tyr Arg Val Thr Val Ile Thr Ala Val Glu Arg Arg Ile Pro
                325                 330                 335

Gly Leu Pro Asp Arg Arg Gln Arg Gly Gly Ser Arg Leu Arg Pro Asp
            340                 345                 350

Arg Asn Ser Ala Ala Asp Tyr Tyr Ser Ala Leu Arg Ser Asp Ala Glu
        355                 360                 365

Asn Lys Val Ser Ser Ala Val Val Ala Ile Asp Val Lys Thr Gly Ser
    370                 375                 380

Pro Arg Trp Val Phe Gln Thr Ala His Lys Asp Val Trp Asp Tyr Asp
385                 390                 395                 400

```
Ile Gly Ser Gln Ala Thr Leu Met Asp Met Pro Gly Pro Asp Gly Gln
                405                 410                 415

Thr Val Pro Ala Leu Ile Met Pro Thr Lys Arg Gly Gln Thr Phe Val
            420                 425                 430

Leu Asp Arg Arg Thr Gly Lys Pro Ile Leu Pro Val Glu Glu Arg Pro
        435                 440                 445

Ala Pro Ser Pro Gly Val Ile Pro Gly Asp Pro Arg Ser Pro Thr Gln
    450                 455                 460

Pro Trp Ser Val Gly Met Pro Ala Leu Arg Val Pro Asp Leu Lys Glu
465                 470                 475                 480

Thr Asp Met Trp Gly Met Ser Pro Ile Asp Gln Leu Phe Cys Arg Ile
                485                 490                 495

Lys Phe Arg Arg Ala Asn Tyr Val Gly Glu Phe Thr Pro Pro Ser Val
            500                 505                 510

Asp Lys Pro Trp Ile Glu Tyr Pro Gly Tyr Asn Gly Gly Ser Asp Trp
        515                 520                 525

Gly Ser Met Ser Tyr Asp Pro Gln Ser Gly Ile Leu Ile Ala Asn Trp
    530                 535                 540

Asn Ile Thr Pro Met Tyr Asp Gln Leu Val Thr Arg Lys Lys Ala Asp
545                 550                 555                 560

Ser Leu Gly Leu Met Pro Ile Asp Asp Pro Asn Phe Lys Pro Gly Gly
                565                 570                 575

Gly Gly Ala Glu Gly Asn Gly Ala Met Asp Gly Thr Pro Tyr Gly Ile
            580                 585                 590

Val Val Thr Pro Phe Trp Asp Gln Tyr Thr Gly Met Met Cys Asn Arg
        595                 600                 605

Pro Pro Tyr Gly Met Ile Thr Ala Ile Asp Met Lys His Gly Gln Lys
    610                 615                 620

Val Leu Trp Gln His Pro Leu Gly Thr Ala Arg Ala Asn Gly Pro Trp
625                 630                 635                 640

Gly Leu Pro Thr Gly Leu Pro Trp Glu Ile Gly Thr Pro Asn Asn Gly
                645                 650                 655

Gly Ser Val Val Thr Gly Gly Leu Ile Phe Ile Gly Ala Ala Thr
            660                 665                 670

Asp Asn Gln Ile Arg Ala Ile Asp Glu His Thr Gly Lys Val Val Trp
        675                 680                 685

Ser Ala Val Leu Pro Gly Gly Gln Ala Asn Pro Met Thr Tyr Glu
    690                 695                 700

Ala Asn Gly His Gln Tyr Val Ala Ile Ala Gly Gly His His Phe Met
705                 710                 715                 720

Met Thr Pro Val Ser Asp Gln Leu Val Val Tyr Ala Leu Pro Asp Ala
                725                 730                 735

Ile Lys Gln

<210> SEQ ID NO 3
<211> LENGTH: 126
<212> TYPE: PRT
<213> ORGANISM: Gluconobacter suboxydans

<400> SEQUENCE: 3

Met Pro Asn Leu Gln Gly Asn Arg Thr Leu Thr Glu Trp Leu Thr Leu
 1               5                  10                  15

Leu Leu Gly Val Ile Val Leu Val Gly Leu Phe Phe Val Ile Gly
            20                  25                  30
```

```
Gly Ala Asp Leu Ala Met Leu Gly Gly Ser Thr Tyr Tyr Val Leu Cys
         35                  40                  45

Gly Ile Leu Leu Val Ala Ser Gly Val Phe Met Leu Met Gly Arg Thr
     50                  55                  60

Leu Gly Ala Phe Leu Tyr Leu Gly Ala Leu Ala Tyr Thr Trp Val Trp
 65                  70                  75                  80

Ser Phe Trp Glu Val Gly Phe Ser Pro Ile Asp Leu Leu Pro Arg Ala
                 85                  90                  95

Phe Gly Pro Thr Ile Leu Gly Ile Leu Val Ala Leu Thr Ile Pro Val
             100                 105                 110

Leu Arg Arg Met Glu Ser Arg Arg Thr Leu Arg Gly Ala Val
         115                 120                 125

<210> SEQ ID NO 4
<211> LENGTH: 8
<212> TYPE: PRT
<213> ORGANISM: Gluconobacter suboxydans
<220> FEATURE:
<221> NAME/KEY: UNSURE
<222> LOCATION: (7)

<400> SEQUENCE: 4

Lys Trp Ala Glu Glu Thr Xaa Pro
 1               5

<210> SEQ ID NO 5
<211> LENGTH: 24
<212> TYPE: PRT
<213> ORGANISM: Gluconobacter suboxydans
<220> FEATURE:
<221> NAME/KEY: UNSURE
<222> LOCATION: (22)

<400> SEQUENCE: 5

Lys Ser Gln Ser Tyr Phe Ala Gly Pro Ser Gln Tyr Ala Pro Gln Ala
 1               5                  10                  15

Pro Gly Val Asn Ala Xaa Asn Leu
             20

<210> SEQ ID NO 6
<211> LENGTH: 16
<212> TYPE: PRT
<213> ORGANISM: Gluconobacter suboxydans
<220> FEATURE:
<221> NAME/KEY: UNSURE
<222> LOCATION: (13)

<400> SEQUENCE: 6

Lys Val Leu Trp Gln His Pro Leu Gly Thr Ala Arg Xaa Asn Gly Pro
 1               5                  10                  15

<210> SEQ ID NO 7
<211> LENGTH: 30
<212> TYPE: PRT
<213> ORGANISM: Gluconobacter suboxydans

<400> SEQUENCE: 7

Gln Phe Ala Pro Ala Gly Ala Gly Gly Glu Pro Ser Ser Ser Val Pro
 1               5                  10                  15

Gly Pro Gly Asn Ala Ser Glu Pro Thr Glu Asn Ser Pro Lys
             20                  25                  30
```

```
<210> SEQ ID NO 8
<211> LENGTH: 24
<212> TYPE: PRT
<213> ORGANISM: Gluconobacter suboxydans

<400> SEQUENCE: 8

Met Arg Arg Pro Tyr Leu Leu Ala Thr Ala Ala Gly Leu Ala Leu Ala
  1               5                  10                  15

Cys Ser Pro Leu Ile Ala His Ala
             20

<210> SEQ ID NO 9
<211> LENGTH: 6
<212> TYPE: PRT
<213> ORGANISM: Gluconobacter suboxydans

<400> SEQUENCE: 9

Pro Asp Ala Ile Lys Gln
  1               5
```